(12) United States Patent
Foerster

(10) Patent No.: US 7,695,494 B2
(45) Date of Patent: *Apr. 13, 2010

(54) METHOD AND APPARATUS FOR ATTACHING CONNECTIVE TISSUES TO BONE USING A KNOTLESS SUTURE ANCHORING DEVICE

(75) Inventor: Seth A. Foerster, San Clemente, CA (US)

(73) Assignee: ArthroCare Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/879,663

(22) Filed: Jun. 29, 2004

(65) Prior Publication Data
US 2004/0260345 A1 Dec. 23, 2004

Related U.S. Application Data

(60) Division of application No. 09/876,488, filed on Jun. 7, 2001, now Pat. No. 6,770,076, and a continuation-in-part of application No. 09/781,793, filed on Feb. 12, 2001.

(60) Provisional application No. 60/273,137, filed on Mar. 2, 2001.

(51) Int. Cl.
*A61B 17/04* (2006.01)
(52) U.S. Cl. ............... 606/232; 606/323; 606/326
(58) Field of Classification Search ........ 606/232, 606/72, 74, 301, 303, 323, 326, 327, 300
See application file for complete search history.

(56) References Cited

U.S. PATENT DOCUMENTS 918,570 A 4/1909 Mather .............. 292/318

(Continued)

FOREIGN PATENT DOCUMENTS

DE 3509417 9/1986

(Continued)

OTHER PUBLICATIONS

European Search Report; relating to EP Application 02742470.4-2318.

(Continued)

*Primary Examiner*—Darwin P Erezo
(74) *Attorney, Agent, or Firm*—Matthew Scheele; Brian E. Szymczak

(57) ABSTRACT

A device for attaching connective tissue to bone has a longitudinal axis and comprises an annular toggle member and a body member disposed distally of the toggle member, such that there is an axial space between the toggle member and the body member. The toggle member is movable between an undeployed position wherein the toggle member has a smaller profile in a direction transverse to the axis and a deployed position wherein the toggle member has a larger profile in the direction transverse to the axis. When installed in a desired procedural site, in suitable bone, suturing material extends axially through a center aperture in the annular toggle member, without being secured to or contacting the toggle member. This approach permits a suture attachment which lies entirely beneath the cortical bone surface, and which further permit the attachment of suture to the bone anchor without the necessity for tying knots, which is particularly arduous and technically demanding in the case of arthroscopic procedures.

11 Claims, 20 Drawing Sheets

U.S. PATENT DOCUMENTS

| | | | |
|---|---|---|---|
| 1,153,053 A | 9/1915 | Forster | 43/44.85 |
| 1,565,041 A | 12/1925 | Arneu | 24/129 R |
| 2,269,963 A | 1/1942 | Wrapler | 604/604 |
| 2,485,531 A | 10/1949 | Dzus et al. | 128/92 |
| 2,600,395 A | 6/1952 | Domoj et al. | 87/13 |
| 3,143,916 A | 8/1964 | Rice | 85/71 |
| 3,942,407 A | 3/1976 | Mortensen | 85/71 |
| 3,946,740 A | 3/1976 | Bassett | 128/334 |
| 3,994,521 A | 11/1976 | Van Gompel | 292/319 |
| 4,047,533 A | 9/1977 | Perciaccante et al. | 128/335.5 |
| 4,109,658 A | 8/1978 | Hughes | 128/340 |
| 4,186,921 A | 2/1980 | Fox | 29/461 |
| 4,210,148 A | 7/1980 | Stivala | 606/232 |
| 4,274,324 A | 6/1981 | Giannuzzi | 411/38 |
| 4,301,551 A | 11/1981 | Dore et al. | 623/13.3 |
| 4,319,428 A | 3/1982 | Fox | 47/42 |
| 4,345,339 A | 8/1982 | Muller et al. | 623/13.2 |
| 4,345,601 A | 8/1982 | Fukuda | 128/339 |
| 4,373,530 A | 2/1983 | Kilejian | 128/334 R |
| 4,384,389 A | 5/1983 | Sato | 24/136 K |
| 4,409,974 A | 10/1983 | Freedland | 128/92 |
| 4,456,270 A | 6/1984 | Zettl et al. | 279/62 |
| 4,467,478 A | 8/1984 | Jurgutis | 606/75 |
| 4,483,023 A | 11/1984 | Hoffman, Jr. et al. | 623/13.15 |
| 4,493,323 A | 1/1985 | Albright et al. | 128/340 |
| 4,580,936 A | 4/1986 | Francis et al. | 411/38 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | |
| 4,672,957 A | 6/1987 | Hourahane | 606/80 |
| 4,680,835 A | 7/1987 | Horng | 24/712.5 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,750,492 A | 6/1988 | Jacobs | 606/230 |
| 4,772,286 A | 9/1988 | Goble et al. | 623/13.14 |
| 4,779,616 A | 10/1988 | Johnson et al. | 606/148 |
| 4,792,336 A | 12/1988 | Hlavacek et al. | 623/13.18 |
| 4,809,408 A | 3/1989 | Abrahamson | 24/136 K |
| 4,823,780 A | 4/1989 | Odensten et al. | 606/96 |
| 4,828,439 A | 5/1989 | Giannuzzi | 411/37 |
| 4,834,755 A | 5/1989 | Silverstrini et al. | 623/13.19 |
| 4,851,005 A | 7/1989 | Hunt et al. | 623/13 |
| 4,870,957 A | 10/1989 | Goble et al. | 606/73 |
| 4,917,700 A | 4/1990 | Aikins | 623/13.19 |
| 4,926,860 A | 5/1990 | Stice et al. | 606/144 |
| 4,935,027 A | 6/1990 | Yoon | 606/146 |
| 4,946,377 A | 8/1990 | Kovach | 623/13.18 |
| 4,946,467 A | 8/1990 | Ohi et al. | 606/228 |
| 4,946,468 A | 8/1990 | Li | 606/232 |
| 4,957,498 A | 9/1990 | Caspari | 606/146 |
| 4,962,929 A | 10/1990 | Melton, Jr. | 473/516 |
| 4,968,315 A | 11/1990 | Gatturna | 606/72 |
| 4,981,149 A | 1/1991 | Yoon et al. | 128/898 |
| 4,987,665 A | 1/1991 | Dumican | 28/218 |
| 5,002,550 A * | 3/1991 | Li | 606/139 |
| 5,019,093 A | 5/1991 | Kaplan et al. | 606/228 |
| 5,037,422 A | 8/1991 | Hayhurst et al. | |
| 5,046,513 A * | 9/1991 | Gatturna et al. | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | |
| 5,195,542 A | 3/1993 | Gazielly et al. | 60/244 |
| 5,203,787 A | 4/1993 | Noblitt et al. | 606/232 |
| RE34,293 E | 6/1993 | Goble et al. | 623/13.14 |
| 5,217,495 A | 6/1993 | Kaplan et al. | 623/13.18 |
| 5,219,359 A | 6/1993 | McQuilkin et al. | 606/232 |
| 5,224,946 A | 7/1993 | Hayhurst et al. | |
| 5,258,016 A | 11/1993 | DiPoto et al. | 606/232 |
| 5,259,846 A | 11/1993 | Granger et al. | 606/224 |
| 5,263,984 A | 11/1993 | Li | 623/13.18 |
| 5,275,176 A | 1/1994 | Chandler | 606/242 |
| 5,304,184 A | 4/1994 | Hathaway et al. | 606/144 |
| 5,318,575 A | 6/1994 | Chesterfield et al. | 606/151 |
| 5,324,308 A | 6/1994 | Pierce | |
| 5,326,205 A | 7/1994 | Anspach, III et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A | 10/1994 | Lee et al. | |
| 5,364,407 A | 11/1994 | Poll | 606/139 |
| 5,376,118 A | 12/1994 | Kaplan et al. | 623/23.72 |
| 5,383,905 A | 1/1995 | Golds et al. | |
| 5,405,352 A | 4/1995 | Weston | 606/148 |
| 5,405,359 A | 4/1995 | Pierce | |
| 5,413,579 A | 5/1995 | Tom Du Toit | 606/87 |
| 5,417,691 A | 5/1995 | Hayhurst | 606/72 |
| 5,417,699 A | 5/1995 | Klein et al. | 606/139 |
| 5,417,712 A | 5/1995 | Whitaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | |
| 5,470,335 A | 11/1995 | DuToit | 606/73 |
| 5,472,452 A | 12/1995 | Trott | |
| 5,480,403 A | 1/1996 | Lee et al. | |
| 5,486,197 A * | 1/1996 | Le et al. | 606/232 |
| 5,499,991 A | 3/1996 | Garman et al. | 606/148 |
| 5,501,683 A | 3/1996 | Trott | |
| 5,501,695 A * | 3/1996 | Anspach et al. | 606/232 |
| 5,505,735 A * | 4/1996 | Li | 606/72 |
| 5,514,159 A | 5/1996 | Matula et al. | 606/232 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,763 A | 7/1996 | Mastri et al. | 606/148 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | |
| 5,569,305 A | 10/1996 | Bonutti | 606/232 |
| 5,569,306 A * | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A * | 12/1996 | Greenfield | 606/73 |
| 5,584,839 A | 12/1996 | Gieringer | 606/96 |
| 5,584,860 A | 12/1996 | Goble et al. | 606/232 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | |
| 5,609,597 A | 3/1997 | Lehrer | 606/139 |
| 5,611,801 A | 3/1997 | Songer | 606/73 |
| 5,613,974 A | 3/1997 | Andreas et al. | 606/144 |
| 5,618,290 A | 4/1997 | Toy et al. | 606/139 |
| 5,618,314 A | 4/1997 | Harwin et al. | 606/232 |
| 5,626,614 A | 5/1997 | Hart | 606/232 |

| Patent No. | Kind | Date | Inventor | Class |
|---|---|---|---|---|
| 5,630,824 | A | 5/1997 | Hart | 606/139 |
| 5,632,748 | A | 5/1997 | Beck, Jr. et al. | 606/72 |
| 5,645,589 | A | 7/1997 | Li | 623/16 |
| 5,647,874 | A | 7/1997 | Hayhurst | 606/72 |
| 5,649,940 | A | 7/1997 | Hart et al. | 606/148 |
| 5,658,313 | A | 8/1997 | Thal | 606/232 |
| 5,665,110 | A | 9/1997 | Chervitz et al. | 606/232 |
| 5,665,112 | A | 9/1997 | Thal | 606/232 |
| 5,667,528 | A | 9/1997 | Colligan | 606/224 |
| D385,352 | S | 10/1997 | Bales et al. | D24/145 |
| 5,681,333 | A | 10/1997 | Burkhart et al. | 606/148 |
| 5,681,351 | A | 10/1997 | Jamiolkowski et al. | |
| 5,683,417 | A | 11/1997 | Cooper | 606/223 |
| 5,683,418 | A | 11/1997 | Luscombe et al. | 606/232 |
| 5,683,419 | A | 11/1997 | Thal | 606/232 |
| 5,690,649 | A | 11/1997 | Li | 606/139 |
| 5,693,060 | A | 12/1997 | Martin | 606/148 |
| 5,697,950 | A | 12/1997 | Fucci et al. | 606/232 |
| 5,702,397 | A * | 12/1997 | Goble et al. | 606/72 |
| 5,702,398 | A | 12/1997 | Tarabishy | |
| 5,707,362 | A | 1/1998 | Yoon | 604/164 |
| 5,707,394 | A | 1/1998 | Miller et al. | 606/232 |
| 5,709,708 | A * | 1/1998 | Thal | 606/232 |
| 5,720,765 | A | 2/1998 | Thal | |
| 5,725,529 | A | 3/1998 | Nicholson et al. | 606/72 |
| 5,725,541 | A | 3/1998 | Anspach, III et al. | 606/151 |
| 5,728,136 | A | 3/1998 | Thal | |
| 5,733,307 | A | 3/1998 | Dinsdale | 606/232 |
| 5,741,281 | A | 4/1998 | Martin | 606/148 |
| 5,741,282 | A | 4/1998 | Anspach, III et al. | 606/151 |
| 5,766,250 | A | 6/1998 | Chervitz et al. | |
| 5,782,863 | A | 7/1998 | Bartlett | |
| 5,782,864 | A | 7/1998 | Lizardi | |
| 5,782,865 | A | 7/1998 | Grotz | 606/72 |
| 5,791,899 | A | 8/1998 | Sachdeva | 433/173 |
| 5,792,152 | A | 8/1998 | Klein et al. | 606/144 |
| 5,797,927 | A | 8/1998 | Yoon | 606/144 |
| 5,797,963 | A | 8/1998 | McDevitt | 606/232 |
| 5,810,848 | A | 9/1998 | Hayhurst | 606/144 |
| 5,810,854 | A | 9/1998 | Beach | 606/232 |
| 5,814,052 | A | 9/1998 | Nakao et al. | 606/148 |
| 5,814,056 | A | 9/1998 | Prosst et al. | 606/151 |
| 5,814,071 | A | 9/1998 | McDevitt et al. | 606/232 |
| 5,814,072 | A | 9/1998 | Bonutti | 606/232 |
| 5,843,111 | A | 12/1998 | Vijfvinkel | 606/171 |
| 5,849,004 | A | 12/1998 | Bramlet | 606/232 |
| 5,860,978 | A | 1/1999 | McDevitt | 606/72 |
| 5,860,991 | A | 1/1999 | Klein et al. | 606/144 |
| 5,860,992 | A | 1/1999 | Daniel et al. | 606/145 |
| 5,868,789 | A | 2/1999 | Heubner | 606/232 |
| 5,879,372 | A | 3/1999 | Bartlett | 606/232 |
| 5,882,340 | A | 3/1999 | Yoon | 604/164 |
| 5,885,294 | A | 3/1999 | Pedlick et al. | 606/80 |
| 5,891,168 | A | 4/1999 | Thal | 606/232 |
| 5,893,850 | A | 4/1999 | Cachia | 606/72 |
| 5,902,311 | A | 5/1999 | Andreas et al. | 606/144 |
| 5,904,692 | A | 5/1999 | Steckel et al. | 606/139 |
| 5,911,721 | A | 6/1999 | Nicholson et al. | |
| 5,921,994 | A | 7/1999 | Andreas et al. | 606/144 |
| 5,935,107 | A | 8/1999 | Taylor et al. | 604/164 |
| 5,935,129 | A | 8/1999 | McDevitt et al. | |
| 5,941,900 | A | 8/1999 | Bonutti | 606/232 |
| 5,941,901 | A | 8/1999 | Egan | |
| 5,944,724 | A | 8/1999 | Lizardi | 606/104 |
| 5,944,739 | A | 8/1999 | Zlock et al. | 606/232 |
| 5,947,982 | A | 9/1999 | Duran | 606/139 |
| 5,948,000 | A | 9/1999 | Larsen et al. | |
| 5,948,001 | A | 9/1999 | Larsen | |
| 5,957,953 | A | 9/1999 | DiPoto et al. | 606/232 |
| 5,957,968 | A | 9/1999 | Belden et al. | 607/126 |
| 5,961,530 | A | 10/1999 | Moore et al. | 606/148 |
| 5,961,538 | A | 10/1999 | Pedlick et al. | |
| 5,968,044 | A | 10/1999 | Nicholson et al. | |
| 5,980,558 | A | 11/1999 | Wiley | 606/232 |
| 5,980,559 | A | 11/1999 | Bonutti | 606/232 |
| 5,984,933 | A | 11/1999 | Yoon | 606/148 |
| 5,993,459 | A | 11/1999 | Larsen et al. | |
| 6,001,104 | A | 12/1999 | Benderev et al. | 606/80 |
| 6,001,109 | A | 12/1999 | Kontos | 606/148 |
| 6,007,566 | A | 12/1999 | Wenstrom, Jr. | |
| 6,007,567 | A | 12/1999 | Bonutti | 606/232 |
| 6,010,525 | A | 1/2000 | Bonutti et al. | 606/232 |
| 6,013,083 | A | 1/2000 | Bennett | 606/104 |
| 6,017,346 | A | 1/2000 | Grotz | 606/72 |
| 6,022,360 | A | 2/2000 | Reimels et al. | 606/144 |
| 6,022,373 | A | 2/2000 | Li | 606/232 |
| 6,024,758 | A | 2/2000 | Thal | |
| 6,033,430 | A | 3/2000 | Bonutti | 606/232 |
| 6,036,699 | A | 3/2000 | Andreas et al. | 606/139 |
| 6,045,571 | A | 4/2000 | Hill et al. | 606/228 |
| 6,045,572 | A | 4/2000 | Johnson et al. | 606/232 |
| 6,045,573 | A | 4/2000 | Wenstrom et al. | 606/232 |
| 6,045,574 | A | 4/2000 | Thal | |
| 6,048,351 | A | 4/2000 | Gordon et al. | 606/144 |
| 6,051,006 | A | 4/2000 | Shluzas et al. | 606/148 |
| 6,053,935 | A | 4/2000 | Brenneman et al. | 606/232 |
| 6,056,773 | A * | 5/2000 | Bonutti | 606/232 |
| 6,068,648 | A | 5/2000 | Cole et al. | 606/232 |
| 6,083,243 | A | 7/2000 | Pokropinski et al. | 606/230 |
| 6,086,608 | A * | 7/2000 | Ek et al. | 606/232 |
| 6,096,051 | A | 8/2000 | Kortenbach et al. | 606/144 |
| 6,102,934 | A | 8/2000 | Li | 606/232 |
| 6,117,160 | A | 9/2000 | Bonutti | 606/215 |
| 6,117,161 | A | 9/2000 | Li | 606/232 |
| 6,143,004 | A | 11/2000 | Davis et al. | 606/144 |
| 6,146,386 | A | 11/2000 | Blackman | 606/103 |
| 6,146,406 | A | 11/2000 | Shluzas et al. | |
| 6,149,669 | A | 11/2000 | Li | 606/232 |
| 6,156,039 | A | 12/2000 | Thal | 606/72 |
| 6,156,056 | A | 12/2000 | Kearns et al. | 606/232 |
| 6,159,235 | A | 12/2000 | Kim | |
| 6,162,537 | A | 12/2000 | Martin et al. | 428/373 |
| 6,171,317 | B1 | 1/2001 | Jackson et al. | 606/148 |
| 6,200,329 | B1 | 3/2001 | Fung et al. | 606/232 |
| 6,200,893 | B1 | 3/2001 | Sneh | 438/685 |
| 6,206,895 | B1 | 3/2001 | Levison | |
| 6,217,592 | B1 | 4/2001 | Freda et al. | 606/145 |
| 6,221,107 | B1 | 4/2001 | Steiner et al. | 623/13.14 |
| 6,228,096 | B1 | 5/2001 | Marchand | 606/139 |
| 6,241,736 | B1 | 6/2001 | Sater | 606/104 |
| 6,267,766 | B1 | 7/2001 | Burkhart | 606/72 |
| 6,280,474 | B1 | 8/2001 | Cassidy et al. | 623/16.11 |
| 6,293,961 | B2 | 9/2001 | Schwartz | 606/232 |
| 6,296,659 | B1 | 10/2001 | Foerster | 606/224 |
| 6,315,781 | B1 | 11/2001 | Reinhardt et al. | |
| 6,319,252 | B1 | 11/2001 | McDevitt et al. | |
| 6,319,269 | B1 | 11/2001 | Li | 606/232 |
| 6,319,271 | B1 | 11/2001 | Schwartz | 606/232 |
| 6,328,758 | B1 | 12/2001 | Tornier et al. | 606/232 |
| 6,355,053 | B1 | 3/2002 | Li | |
| 6,409,743 | B1 * | 6/2002 | Fenton, Jr. | 606/232 |
| 6,432,123 | B2 | 8/2002 | Schwartz et al. | 606/232 |
| 6,436,109 | B1 | 8/2002 | Kontos | 606/148 |
| 6,451,030 | B2 | 9/2002 | Li et al. | 606/139 |
| 6,464,713 | B2 | 10/2002 | Bonutti | 606/232 |
| 6,471,715 | B1 | 10/2002 | Weiss | 606/216 |
| 6,475,230 | B1 | 11/2002 | Bonutti et al. | 606/232 |
| 6,491,714 | B1 | 12/2002 | Bennett | 606/232 |
| 6,517,542 | B1 | 2/2003 | Papay et al. | 606/73 |
| 6,520,980 | B1 | 2/2003 | Foerster | 606/232 |
| 6,524,317 | B1 | 2/2003 | Ritchart et al. | 606/72 |
| 6,527,794 | B1 | 3/2003 | McDevitt et al. | |
| 6,540,770 | B1 | 4/2003 | Tornier et al. | 606/232 |
| 6,569,187 | B1 | 5/2003 | Bonutti et al. | 606/232 |
| 6,575,987 | B2 | 6/2003 | Gellman et al. | |
| 6,582,453 | B1 | 6/2003 | Tran et al. | 606/232 |

| | | | |
|---|---|---|---|
| 6,585,730 | B1 | 7/2003 | Foerster et al. |
| 6,635,073 | B2 | 10/2003 | Bonutti ................. 606/232 |
| 6,638,279 | B2 | 10/2003 | Bonutti ................. 606/ 60 |
| 6,645,227 | B2 | 11/2003 | Fallin et al. ................. 606/232 |
| 6,648,903 | B1 | 11/2003 | Pierson, III ................. 606/232 |
| 6,652,561 | B1 * | 11/2003 | Tran ................. 606/232 |
| 6,656,183 | B2 | 12/2003 | Colleran et al. |
| 6,660,008 | B1 * | 12/2003 | Foerster et al. ................. 606/72 |
| 6,660,023 | B2 | 12/2003 | McDevitt et al. |
| 6,679,896 | B2 | 1/2004 | Gellman et al. ................. 606/148 |
| 6,682,549 | B2 * | 1/2004 | Bartlett ................. 606/232 |
| 6,689,154 | B2 * | 2/2004 | Bartlett ................. 606/232 |
| 6,692,516 | B2 | 2/2004 | West et al. ................. 606/232 |
| 6,716,234 | B2 | 4/2004 | Grafton ................. 606/228 |
| 6,736,829 | B1 | 5/2004 | Li et al. ................. 606/232 |
| 6,770,076 | B2 * | 8/2004 | Foerster ................. 606/72 |
| 6,780,198 | B1 | 8/2004 | Gregoire et al. ................. 606/232 |
| 6,855,157 | B2 * | 2/2005 | Foerster et al. ................. 606/232 |
| 6,860,887 | B1 | 3/2005 | Frankie ................. 606/104 |
| 6,972,027 | B2 | 12/2005 | Fallin et al. ................. 606/232 |
| 7,029,490 | B2 | 4/2006 | Grafton et al. ................. 606/228 |
| 7,083,638 | B2 * | 8/2006 | Foerster ................. 606/232 |
| 7,090,690 | B2 | 8/2006 | Foerster et al. ................. 606/232 |
| 7,104,999 | B2 | 9/2006 | Overaker ................. 606/142 |
| 7,150,757 | B2 | 12/2006 | Fallin et al. ................. 606/232 |
| 7,247,164 | B1 | 7/2007 | Ritchart et al. ................. 606/232 |
| 7,285,124 | B2 | 10/2007 | Foerster ................. 606/139 |
| 7,329,272 | B2 | 2/2008 | Burkhart et al. ................. 606/232 |
| 7,615,061 | B2 | 11/2009 | White et al. ................. 606/148 |
| 2001/0008971 | A1 | 7/2001 | Schwartz et al. |
| 2002/0128684 | A1 | 9/2002 | Foerster |
| 2003/0149448 | A1 | 8/2003 | Foerster et al. |
| 2003/0167062 | A1 | 9/2003 | Gambale et al. |
| 2003/0191498 | A1 | 10/2003 | Foerster et al. ................. 606/232 |
| 2003/0195563 | A1 | 10/2003 | Foerster ................. 606/232 |
| 2003/0195564 | A1 | 10/2003 | Tran et al. ................. 606/232 |
| 2004/0093031 | A1 | 5/2004 | Burkhart et al. ................. 606/232 |
| 2004/0138706 | A1 | 7/2004 | Abrams et al. ................. 606/232 |
| 2004/0236336 | A1 | 11/2004 | Foerster et al. ................. 606/72 |
| 2004/0243179 | A1 | 12/2004 | Foerster ................. 606/232 |
| 2005/0033364 | A1 | 2/2005 | Gregoire et al. ................. 606/232 |
| 2005/0080455 | A1 | 4/2005 | Schmieding et al. ........ 606/232 |
| 2005/0090827 | A1 | 4/2005 | Gedebou ................. 606/72 |
| 2005/0240226 | A1 | 10/2005 | Foerster et al. ................. 606/232 |
| 2005/0277986 | A1 | 12/2005 | Foerster ................. 606/232 |
| 2006/0004364 | A1 | 1/2006 | Green et al. ................. 606/72 |
| 2006/0079904 | A1 | 4/2006 | Thal ................. 606/72 |
| 2006/0271060 | A1 | 11/2006 | Gordon ................. 606/232 |
| 2006/0271105 | A1 | 11/2006 | Foerster ................. 606/232 |
| 2006/0293710 | A1 | 12/2006 | Foerster ................. 606/72 |
| 2007/0142838 | A1 | 6/2007 | Jordan ................. 606/75 |
| 2007/0203508 | A1 | 8/2007 | White et al. ................. 606/148 |
| 2008/0015594 | A1 | 1/2008 | Ritchart et al. ................. 606/72 |
| 2008/0051836 | A1 | 2/2008 | Foerster et al. ................. 606/232 |
| 2008/0319478 | A1 | 12/2008 | Foerster et al. ................. 606/148 |
| 2009/0069823 | A1 | 3/2009 | Foerster et al. ................. 606/103 |

FOREIGN PATENT DOCUMENTS

| | | | |
|---|---|---|---|
| DE | 196 28 909 | | 1/1998 |
| EP | 0 535 906 | A2 | 4/1993 |
| EP | 0 571 686 | | 12/1993 |
| EP | 0 611 557 | A2 | 8/1994 |
| EP | 1 072 234 | A2 | 1/2001 |
| EP | 1 072 237 | | 1/2001 |
| FR | 2777442 | | 10/1999 |
| FR | 2777447 | | 10/1999 |
| JP | 2286468 | | 11/1990 |
| JP | 8-52154 | | 2/1996 |
| WO | 89/10096 | | 11/1989 |
| WO | 91/06247 | | 5/1991 |
| WO | WO 95/06439 | | 3/1995 |
| WO | 95/25469 | | 9/1995 |
| WO | 96/17544 | | 6/1996 |
| WO | 97/20522 | | 6/1997 |
| WO | 99/53843 | | 10/1999 |
| WO | 99/53844 | | 10/1999 |
| WO | WO 99/53844 | | 10/1999 |
| WO | WO 02/21997 | | 3/2002 |
| WO | 03/049620 | | 6/2003 |
| WO | 2004/082724 | | 9/2004 |

OTHER PUBLICATIONS

PCT Search Report and Written Opinion for PCT/US06/20657, 7 pages.
PCT Search Report and Written Opinion for PCT/US06/21125 6pgs, mailed May 22, 2008.
PCT International Search Report for PCT/US01/21905 3pgs, mailed Jan. 22, 2002.
PCT International Preliminary Examination Report for PCT/US01/21905 3pgs, Oct. 17, 2003.
PCT International Search Report for PCT/US01/17689 3pgs, mailed Dec. 19, 2001.
PCT International Preliminary Examination Report for PCT/US01/17689 15pgs, Feb. 9, 2003.
PCT International Search Report for PCT/US02/17493 1pg, mailed Mar. 27, 2003.
PCT International Preliminary Examination Report for PCT/US02/17493 4pgs, Sep. 8, 2003.
PCT International Search Report for PCT/US02/41018 2pgs, mailed Jun. 5, 2003.
PCT International Preliminary Examination Report for PCT/US02/41018 3pgs, Feb. 22, 2004.
PCT International Search Report for PCT/US02/04231 1pg, mailed Aug. 14, 2002.
PCT International Preliminary Examination Report for PCT/US02/04231 3pgs, Nov. 13, 2002.
PCT International Search Report for PCT/US03/35695 1pg, mailed Feb. 14, 2005.
PCT International Preliminary Examination Report for PCT/US03/35695 4pgs, Dec. 21, 2005.
EP Partial European Search Report for EP02742470 3pgs, Apr. 13, 2004.
EP Supplementary European Search Report for EP02742470 5pgs, Jul. 30, 2004.
UK Search Report for GB 0816111.9 3 pgs., Dec. 16, 2008.
European Search Report for EP 02734649 3 pgs, Jan. 22, 2009.
Final Office Action mailed Oct. 20, 2008, in related U.S. Appl. No. 10/879,669 9 pgs, Oct. 20, 2008.
Advisory Action mailed Jan. 8, 2009, in related U.S. Appl. No. 10/879,669 3 pgs, Jan. 8, 2009.
Notice of Allowance mailed Apr. 2, 2009, in related U.S. Appl. No. 10/879,669 12 pgs, Apr. 2, 2009.
Non-Final Office Action for U.S. Appl. No. 09/876,488 8pgs, mailed Aug. 27, 2003.
Notice of Allowance for U.S. Appl. No. 09/876,488 7pgs, mailed Mar. 18, 2004.
Final Office Action for U.S. Appl. No. 10/879,669 9pgs, mailed Oct. 20, 2008.
Notice of Allowance for U.S. Appl. No. 10/879,669 11pgs, mailed Apr. 2, 2009.
EP Extended Search Report for EP09162639 4pgs., Oct. 28, 2009.
US 6,238,418, 05/2001, Schwartz et al. (withdrawn)

* cited by examiner

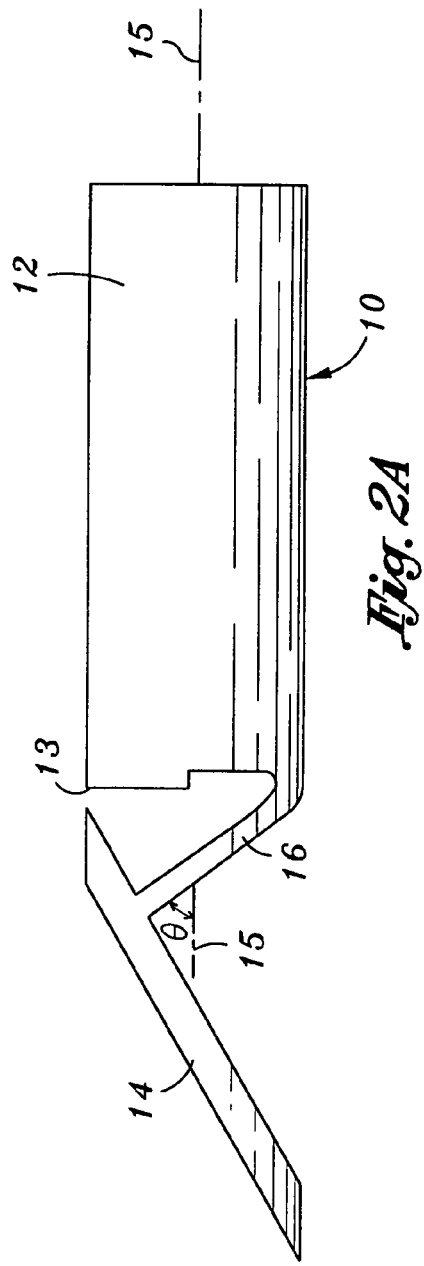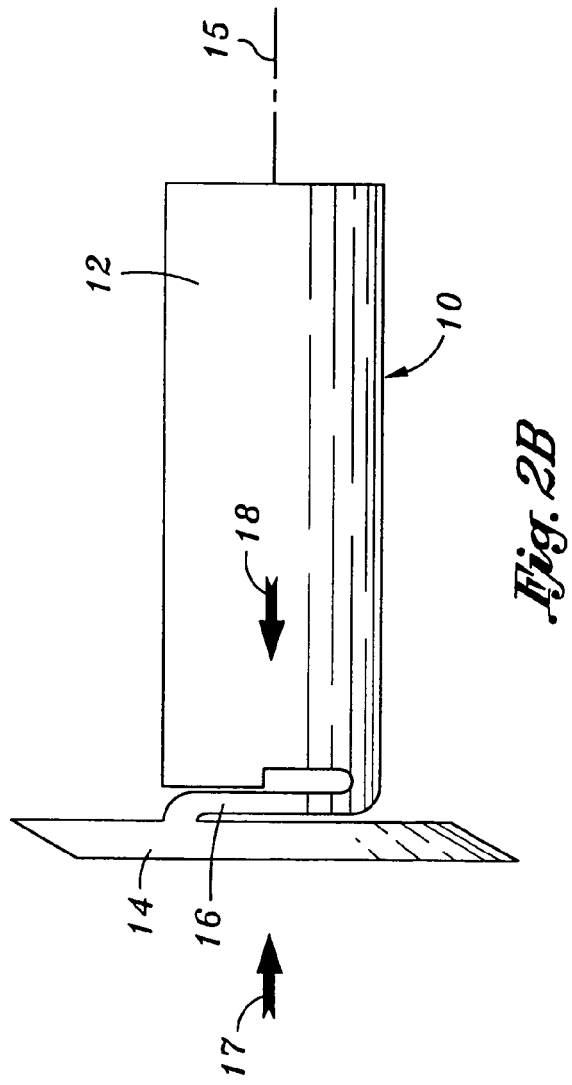

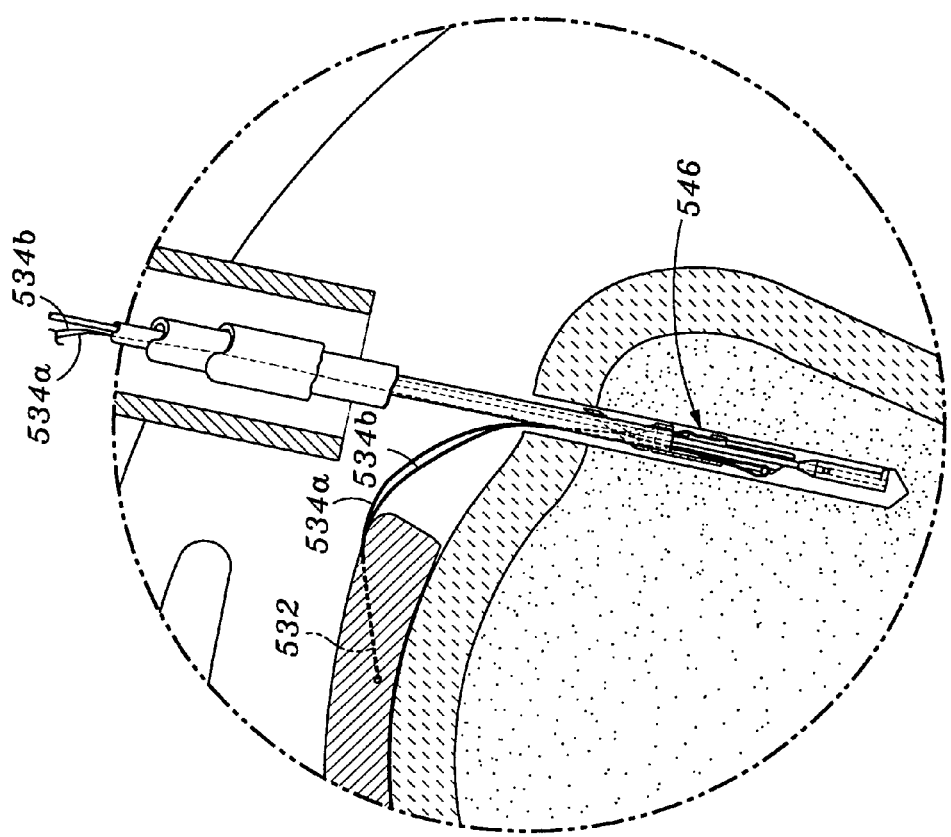
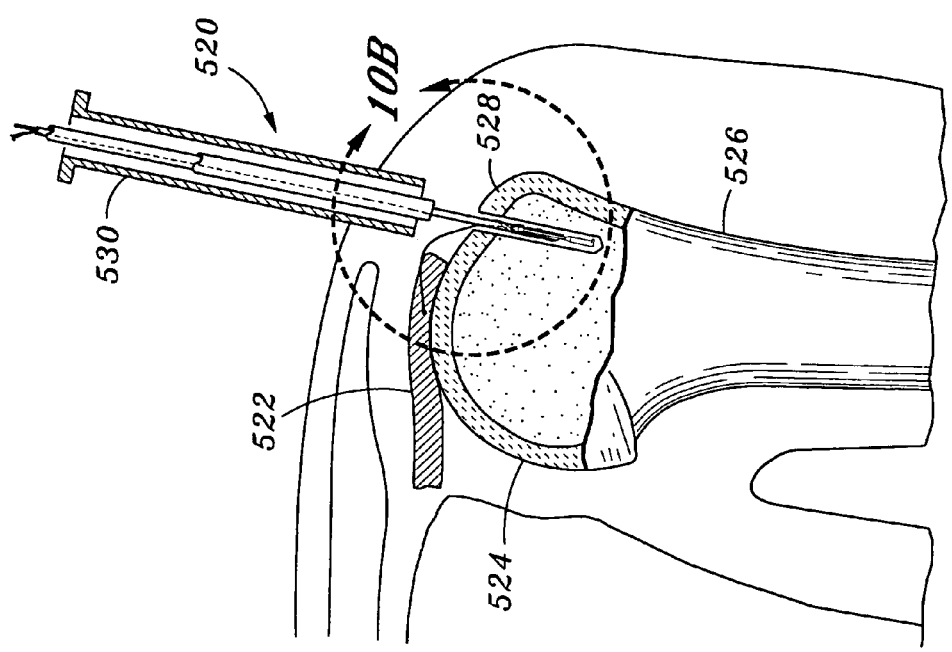

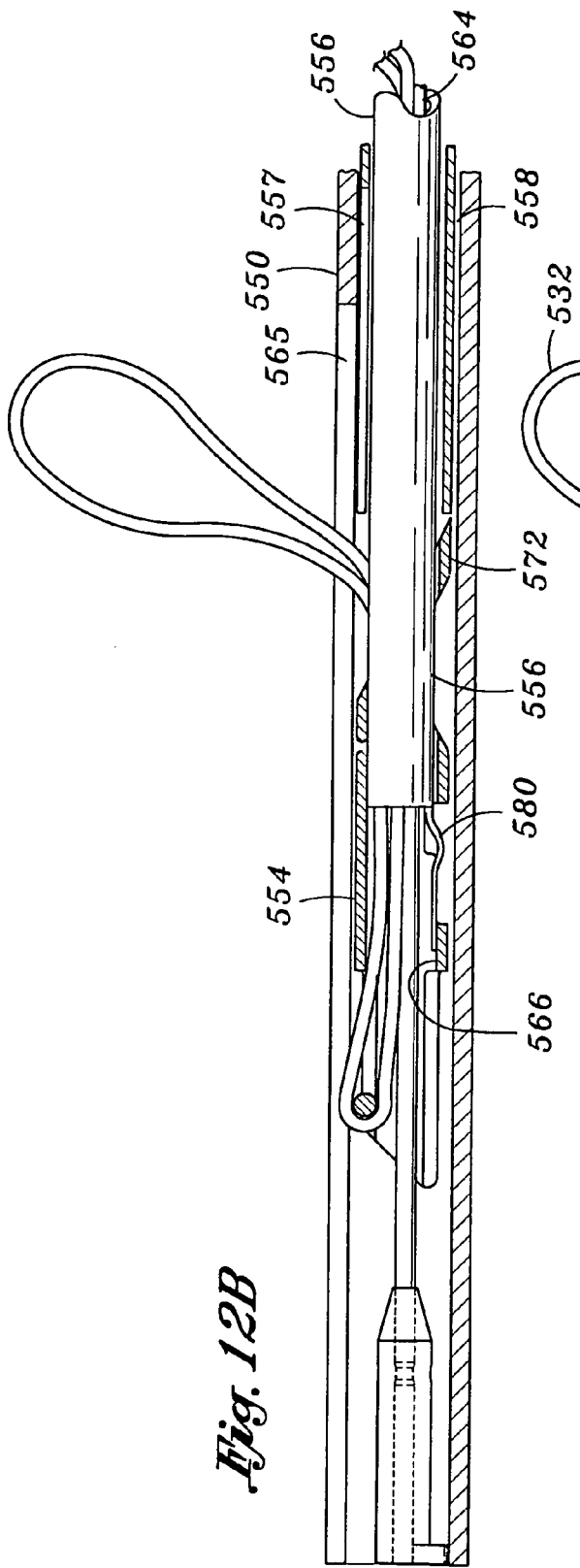
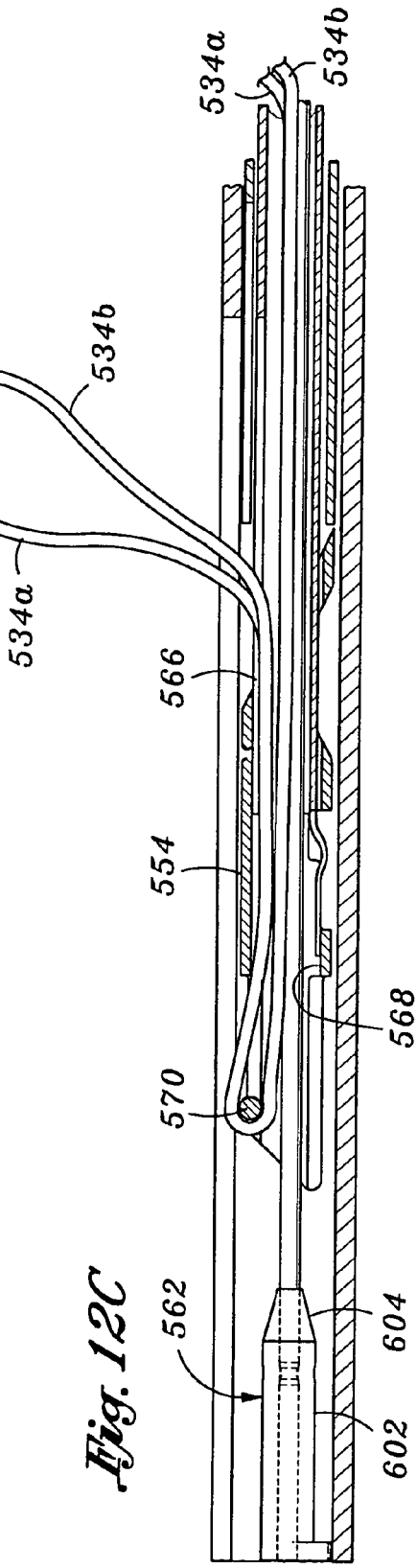

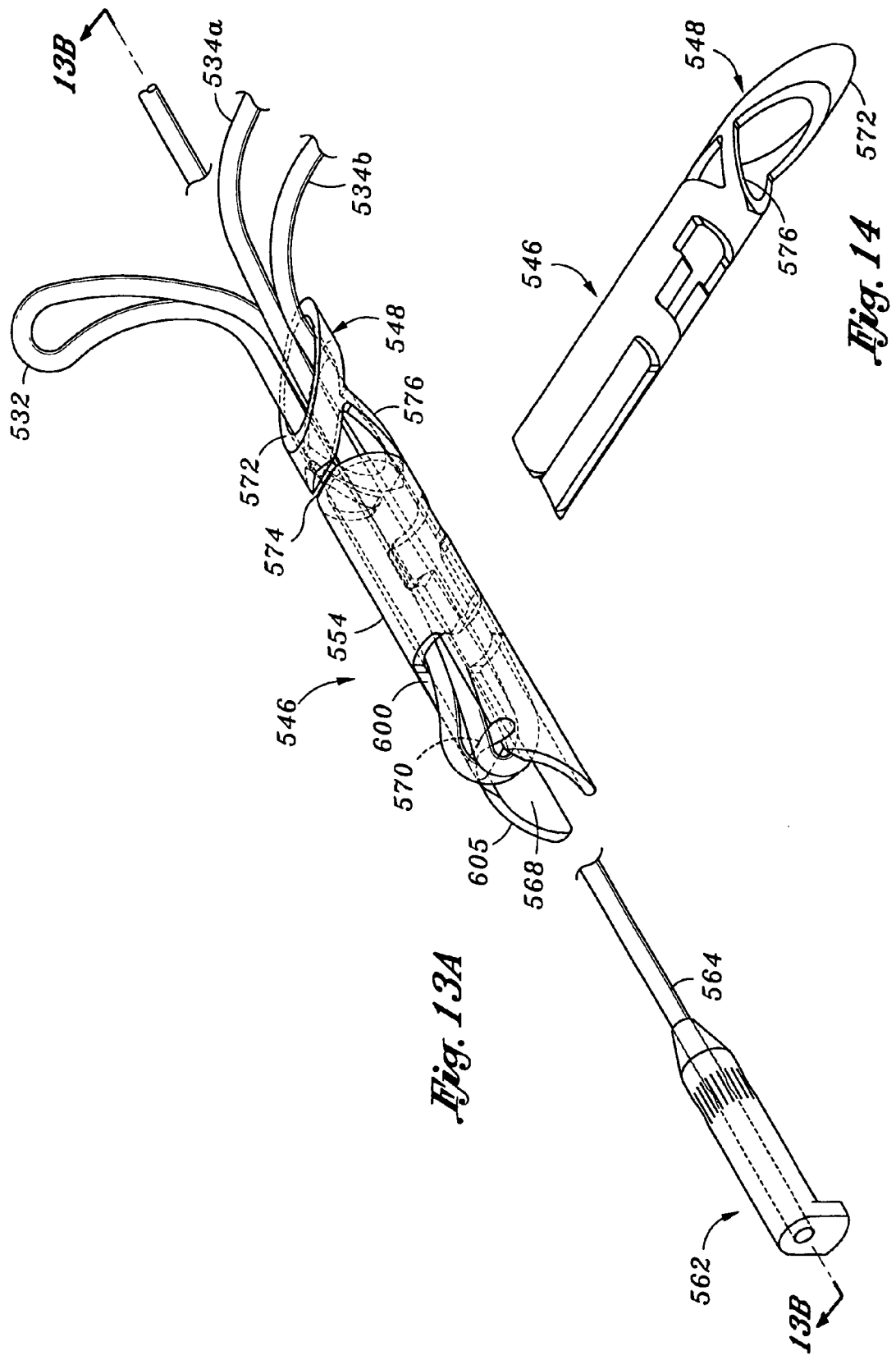

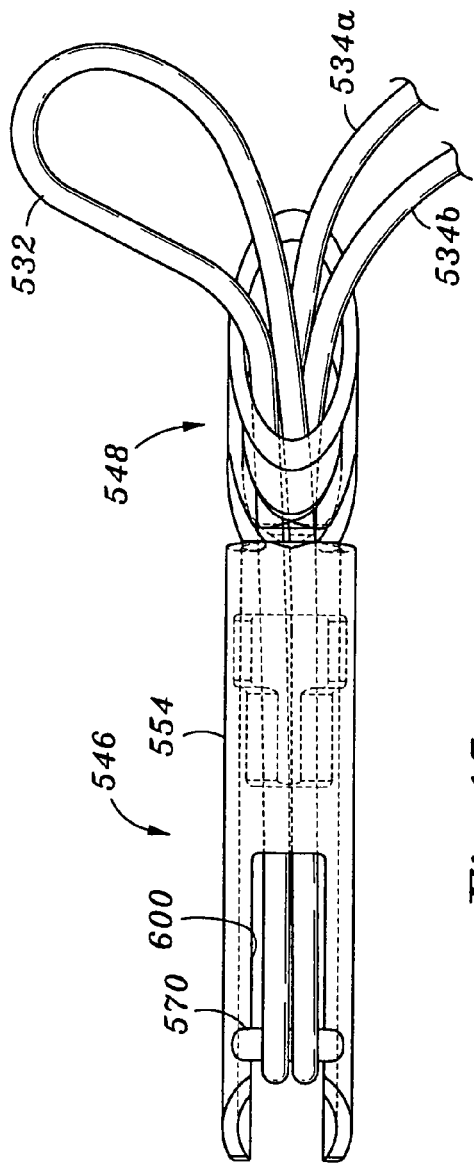
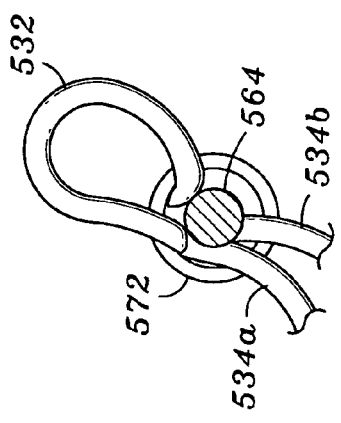
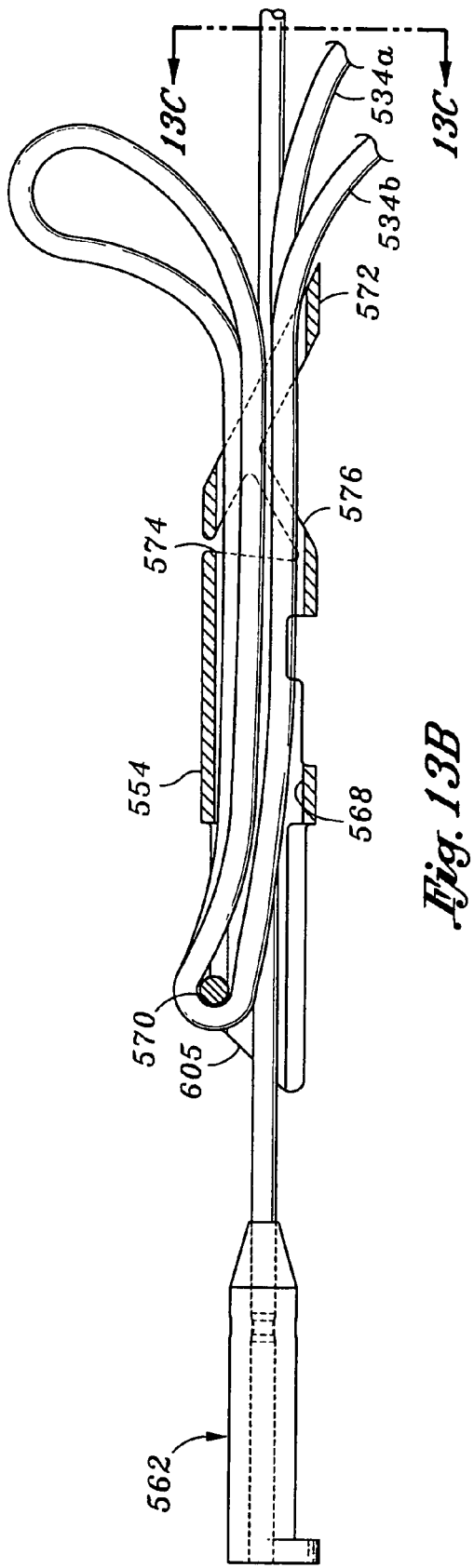

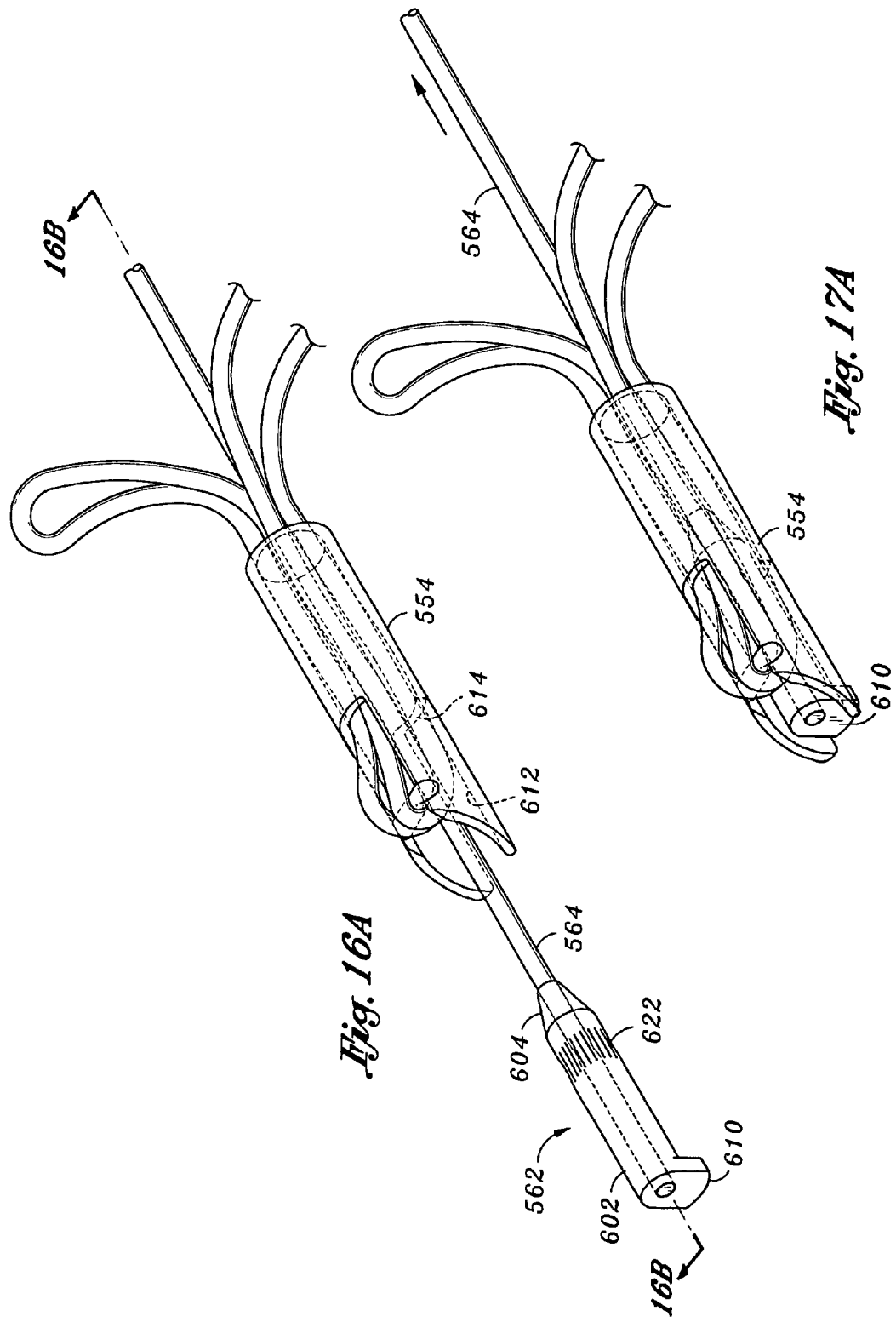

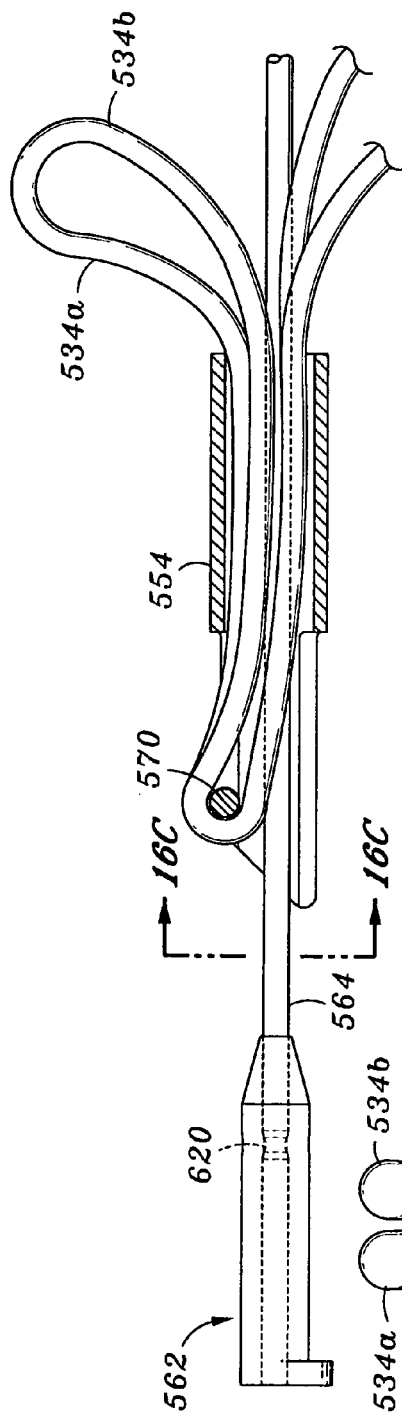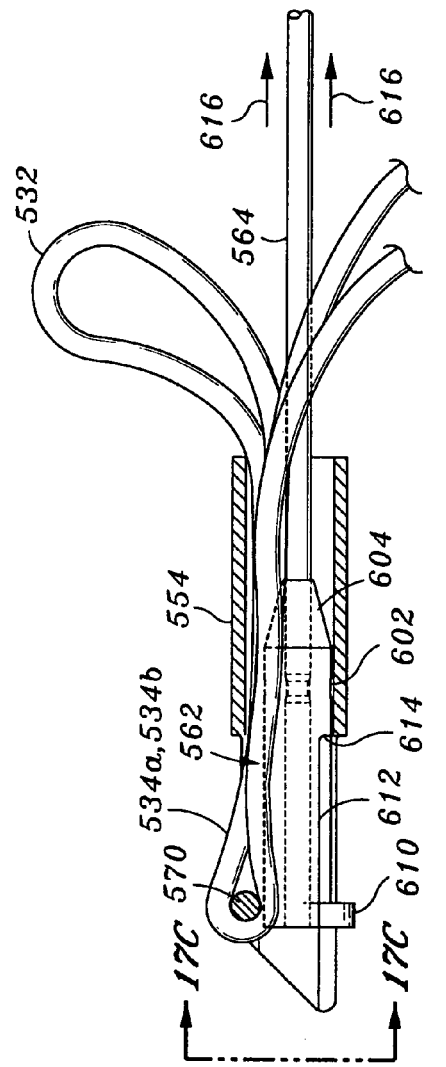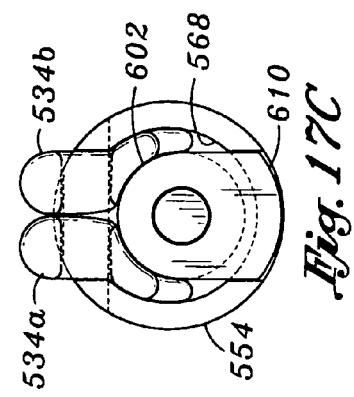

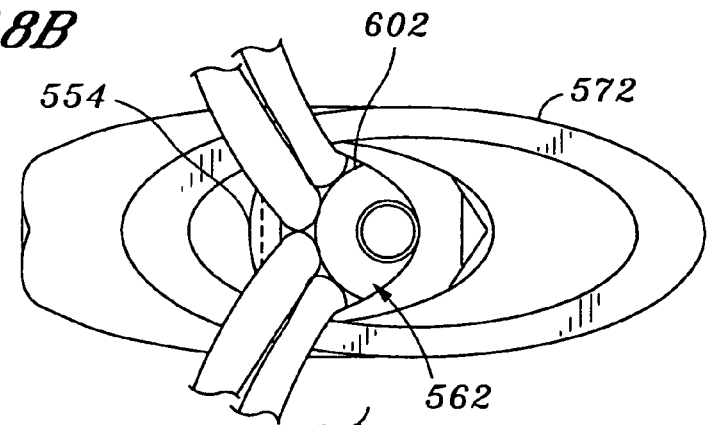
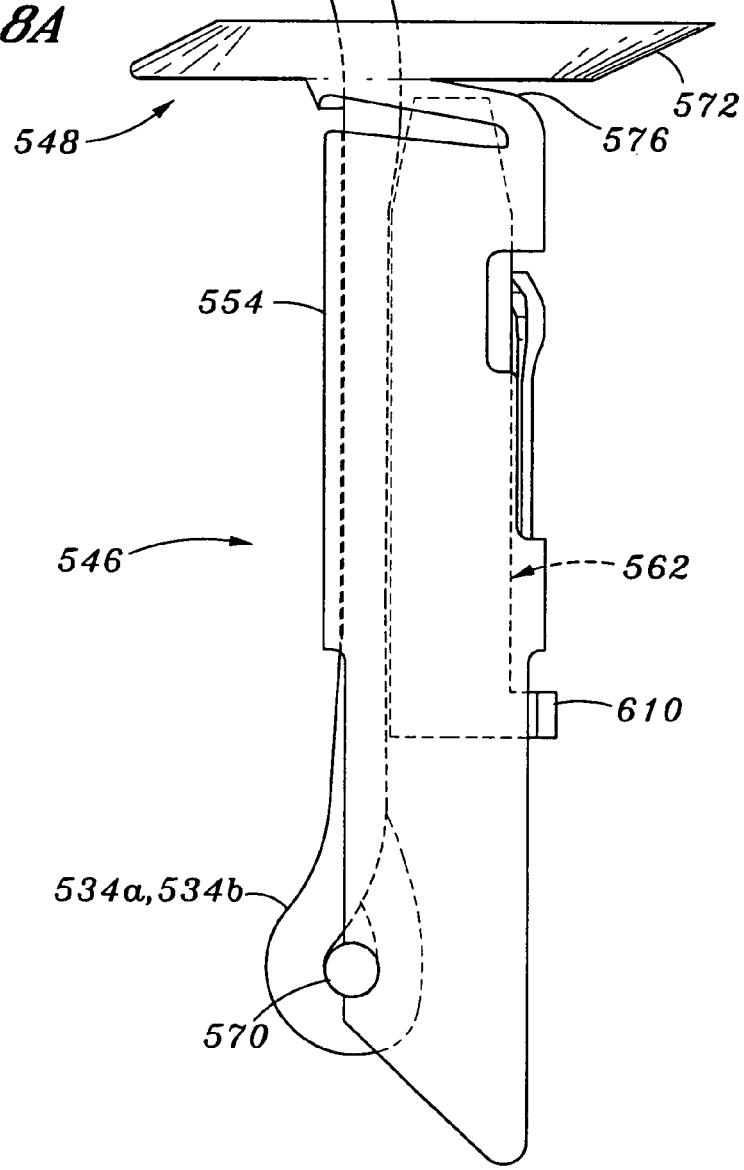

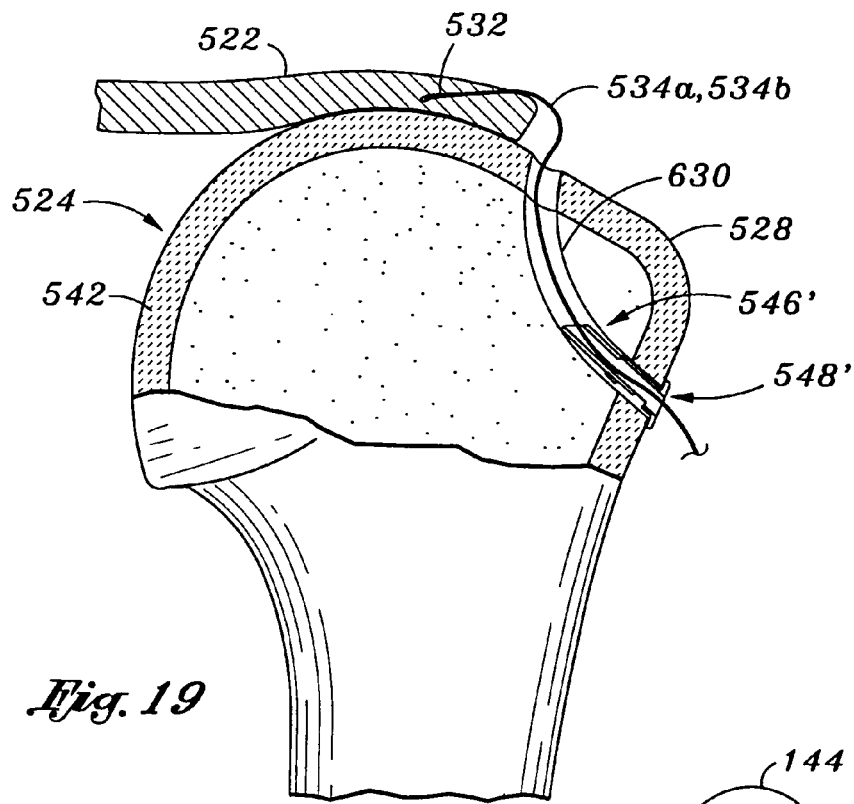
*Fig. 19*
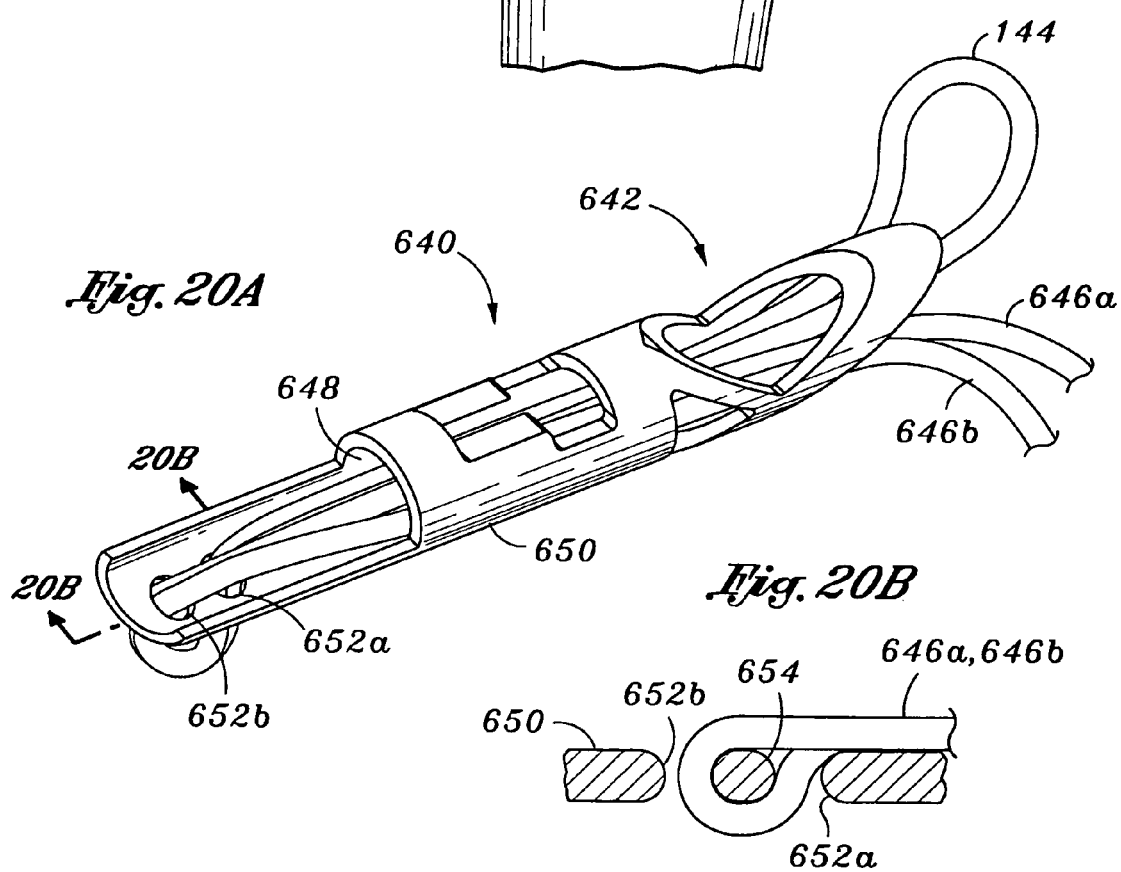
*Fig. 20A*
*Fig. 20B*

METHOD AND APPARATUS FOR ATTACHING CONNECTIVE TISSUES TO BONE USING A KNOTLESS SUTURE ANCHORING DEVICE

This application is a divisional under 35 U.S.C. 120 of U.S. application Ser. No. 09/876,488, filed on Jun. 7, 2001 and now U.S. Pat. No. 6,770,076, which application in turn claims the benefit under 35 U.S.C. 119(e) of the filing date of Provisional Application Ser. No. 60/273,137, filed on Mar. 2, 2001, and is also a continuation-in-part of U.S. application Ser. No. 09/781,793, filed on Feb. 12, 2001, all of which are expressly incorporated by reference herein, and commonly assigned herewith.

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the socalled "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures is of the arthroscopic type, and is considered investigational in nature.

Another significant difficulty with current arthroscopic rotator cuff repair techniques is shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but existing designs suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated $90^\beta$ so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 to Pierce. In this patent, there is disclosed a suture anchor that incorporates a proximal and distal wedge component having inclined mating faces. The distal wedge component has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

A prior art approach that includes tissue attachment is described in U.S. Pat. No. 5,405,359 to Pierce. In this system, a toggle wedge is comprised of a two piece structure comprising a top portion characterized by the presence of a barbed tip and a bottom portion. The suturing material extends through apertures in each of the two toggle portions, and is maintained in position by means of a knot disposed in the suture at a lower edge of the bottom toggle portion. To anchor the suture into adjacent soft tissue, the two toggle portions are rotated relative to one another, as shown for example in FIG. 33. The disclosure states that the device could be used to anchor suture in bone, as well as soft tissue, if two embodiments are utilized in tandem. However, the system is disadvantageous in that it is complex, difficult to manipulate, and still requires the tying of a knot in the suture.

Another approach that includes bone attachment is described in U.S. Pat. No. 5,584,835 to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrot the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock the ball into the race. Although this embodiment purports to be a selflocking anchor adapted for use in blind holes for fixing sutures into bone, the construct shown is complicated, and does not appear to be adequate to reliably fixate the suture.

U.S. Pat. No. 5,782,863 to Bartlett discloses a suture anchor including bone attachment, which simply comprises a conical suture anchor having an anchor bore through which a length of suture is threaded. The anchor is inserted into a bore within a portion of bone using an insertion tool having a shape memory insertion end. As the anchor is inserted, because of its conical shape, it will re-orient itself by rotating in order to fit into the bore, bending the end of the insertion tool. However, once the proximal edge of the bone anchor enters cancellous bone, the shape memory insertion end of the insertion tool will begin resuming its natural straight orientation, thus rotating the anchor back into its original orientation. The corners of the conical body thus protrude into the soft cancellous bone, and the anchor body is prevented from exiting proximally from the bone bore through the hard cortical bone. The insertion tool is then removed.

The Bartlett patent approach, while innovative, is disadvantageous to the extent that it involves the use of a unique and complex insertion tool, and can be difficult to deploy. It also does not permit suturing of the soft tissue prior to anchoring the suture to bone, and thus does not permit tensioning of the suture to approximate the soft tissue to bone, as desired, at the conclusion of the suturing procedure. Additionally, in preferred embodiments, the suture is knotted to the anchor, a known disadvantage.

Yet another prior art approach is disclosed in U.S. Pat. No. 5,961,538 to Pedlick et al. In this patent, a wedge shaped suture anchor system is described for anchoring a length of suture within a bore in a bone portion, which comprises an anchor body having an offset suture opening for receiving the length of suture therethrough, and for creating an imbalance in the rotation of the device as it is inserted. A shaft portion is utilized to insert the wedge-shaped anchor body into the bone bore. Once the anchor body is in cancellous bone, below the cortical bone layer, the shaft is pulled proximally to cause the anchor body to rotate, thereby engaging the corners of the anchor body with the cancellous bone. The shaft then becomes separated from the anchor body, leaving the anchor body in place within the bone.

The Pedlick et al. approach is conventional, in that the suture is attached to desired soft tissue after it is anchored within the bone. Consequently, there is no opportunity to tension the suture, as desired, to optimally approximate the soft tissue to the bone upon completion of the surgical procedure. Additionally, the approach is complex and limited in flexibility, since the suture is directly engaged with the bone anchoring body. There is also the possibility that the bone anchoring body will not sufficiently rotate to firmly become engaged with the cancellous bone before the insertion tool breaks away from the anchor body, in which case it will be impossible to properly anchor the suture.

U.S. Pat. No. 6,056,773 to Bonutti discloses a suture anchoring system which is somewhat similar to that disclosed by Pedlick et al. A cylindrical suture anchor body is provided which is insertable into a bone bore, using a pusher member which pushes distally on the anchor body from a proximal direction. As the anchor body proceeds into the bone bore, below the cortical bone surface, the suture extending through the lumen of the anchor body applies a proximal tensile force on the anchor body, to cause the anchor body to rotate relative to the pusher member, thereby anchoring the anchor body in cancellous bone. Of course, this system has similar disadvantages to those of the Pedlick et al. system, and requires the suture to be directly engaged with the bone anchoring body.

What is needed, therefore, is a new approach for repairing the rotator cuff or fixing other soft tissues to bone, wherein both the bone and suture anchors reside completely below the cortical bone surface, there is no requirement for the surgeon to tie a knot to attach the suture to the bone anchor, and wherein suture tension can be adjusted and possibly measured. The procedure associated with the new approach should better for the patient than existing procedures, should save time, be uncomplicated to use, and be easily taught to practitioners having skill in the art.

SUMMARY OF THE INVENTION

The present invention solves the problems outlined above by providing innovative bone anchor and connective techniques which permit a suture attachment which lies entirely beneath the cortical bone surface, and which further permit the attachment of suture to the bone anchor without the necessity for tying knots, which is particularly arduous and technically demanding in the case of arthroscopic procedures.

More particularly, in one aspect of the invention, a bone anchor device is provided for attaching connective tissue to bone, which has a longitudinal axis and comprises a toggle member and a preferably tubular body member disposed distally of the toggle member. An axial space is present between the toggle member and the body member. A connecting portion is disposed in the axial space, which joins the toggle member to the body member.

In operation, when it is desired to deploy the inventive bone anchor device, the toggle member is movable, in a pivoting or rotational fashion, between an undeployed position wherein the toggle member has a smaller profile in a direction transverse to the longitudinal axis, which is no wider than the transverse dimension or width of the body member and the hole into which the bone anchor device is disposed, and a deployed position wherein the toggle member has a larger profile in the direction transverse to the axis, which is substantially larger than the width of the hole, so that the outer edges of the toggle member become embedded in the cancellous bone which lies beneath the cortical bone surface, and so that there is no reasonable way, short of widening the hole through the cortical bone, of withdrawing the anchor proximally out of the hole.

When the toggle member is deployed, the connecting portion deforms such that the axial space is reduced in length.

The connecting portion preferably comprises a one or more struts having proximal ends joined to the toggle member and distal ends joined to the body member. In manufacture, the body member, struts, and toggle member, which is preferably annular and elliptical in configuration, may all be fabricated from a single piece, such as a hypotube.

Preferably, the inventive toggle member is disposed at an acute angle relative to the axis in the undeployed position, and is disposed in a substantially transverse orientation relative to the axis in the deployed position.

The inventors have discovered that, due to potential cyclic loading effects during usage of the affected body part after completion of the medical procedure, it is advantageous to form at least the connecting portion, and preferably the toggle member as well of a biocompatible relatively ductile material. In a presently preferred embodiment, the material comprises an annealed metal, such as stainless steel.

In a preferred embodiment, there is disposed a mandrel proximally of the toggle member, and a casing extending through the toggle member. The mandrel, together with the body, is useful in actuating the toggle member from its undeployed position to its deployed position.

In another aspect of the invention, there is provided a bone anchor device for attaching soft tissue to bone, which device has a longitudinal axis and comprises a toggle member being rotatable from an undeployed position wherein the toggle member has a smaller profile in a direction transverse to the axis and a deployed position wherein the toggle member has a larger profile in the direction transverse to the axis. The toggle member has no structure for attaching suture material thereto, since the suture material is to be attached to a body member disposed distally of the toggle member.

In yet another aspect of the invention, there is provided an apparatus for attaching connective tissue to bone, which apparatus has a longitudinal axis and comprises an annular toggle member and a body member disposed distally of the toggle member, such that there is an axial space between the toggle member and the body member. Advantageously, the toggle member is movable between an undeployed position wherein the toggle member has a smaller profile in a direction transverse to the axis and a deployed position wherein the toggle member has a larger profile in the direction transverse to the axis. When installed in a desired procedural site, in suitable bone, suturing material extends axially through a center aperture in the annular toggle member, without being secured to or contacting the toggle member.

In still another aspect of the invention, there is provided an apparatus for attaching connective tissue to bone, which apparatus has a longitudinal axis and comprises a toggle member and a body member disposed distally of the toggle member, such that there is an axial space between the toggle member and the body member. The toggle member is movable between an undeployed position wherein the toggle member has a smaller profile in a direction transverse to the axis and a deployed position wherein the toggle member has a larger profile in the direction transverse to the axis. A connecting portion is disposed in the axial space and joins the toggle member to the body member.

In another aspect of the invention, there is provided an apparatus for attaching connective tissue to bone, which comprises an anchor body having a longitudinal axis and having an anchoring structure for fixing the anchor body within a body cavity. The anchor body has a proximal end, a distal end, and a lumen opening at the proximal end, and further includes a suture return member disposed therein such that a length of suture may be introduced into the lumen from the proximal end, looped around the suture return member, and passed out of the lumen through the proximal end. A suture locking plug is movable within the lumen from a first position to a second position, and a bone anchoring member is attached to the anchor body, preferably at the proximal end thereof, and is movable between an undeployed position and a deployed position. In preferred embodiments of the invention, the suture return member comprises a shaft or pin which may be either fixed or rotatable. The bone anchoring member preferably comprises a toggle member, which, in the undeployed position has a smaller profile in a direction transverse to the longitudinal axis and in the deployed position has a larger profile in the direction transverse to the axis.

As noted supra, the toggle member is preferably disposed proximally of the anchor body such that there is an axial space between the toggle member and the anchor body. When the toggle member is moved from the aforementioned undeployed position to the aforementioned deployed position, the axial space is reduced in length. A connecting portion is disposed in the axial space and joins the toggle member to the anchor body. The connecting portion preferably comprises a pair of struts having proximal ends joined to the toggle member and distal ends joined to the anchor body.

In still another aspect of the invention, there is disclosed a method of using suture to secure soft tissue, preferably a tendon, with respect to a body cavity, preferably disposed in a portion of bone. The method comprises the steps of passing a length of suture material through soft tissue so that a loop of suture material is disposed in the soft tissue, resulting in two free ends, and providing an anchor body having an open proximal end and a lumen. A suture return member is disposed in the anchor body. Additional steps include passing the two free ends of the length of suture into the lumen of the anchor body through the open proximal end, and looping them about the suture return member such that the two free ends of the suture extend proximally from the lumen through the open proximal end. The anchor body is fixed with respect to the body cavity, and the loop of suture material is tensioned by pulling on one or both of the two free ends of the length of suture, to approximate the soft tissue with respect to the body cavity as desired. A further step is to fasten the two free ends of the length of suture with respect to the anchor body without knots.

In preferred approaches, the step of fixing the anchor body with respect to the body cavity comprises forming the body cavity, passing the anchor body into the body cavity, and radially expanding anchoring structure, preferably a deployable toggle member, on the anchor body. The anchoring structure is provided on a proximal end of the anchor body so as to engage the cortical layer of the bone and to prevent proximal removal of the anchor body from the body cavity.

In yet another aspect of the invention, there is disclosed a method of securing soft tissue to bone, comprising disposing an anchor body having a longitudinal axis and having a length of suture secured therein within a bore disposed in a portion of bone, and deploying a toggle member attached to a proximal end of the anchor body from an undeployed position wherein the toggle member has a smaller profile in a direction transverse to the axis to a deployed position wherein the toggle member has a larger profile transverse to the axis. The toggle member fixes the anchor body axially relative to the portion of bone. A connecting portion joins the toggle member to the anchor body, and is disposed in an axial space between the toggle member and the anchor body. The aforementioned deploying step includes deforming the connecting portion as the toggle member is moved from the undeployed position to the deployed position.

The invention, together with additional features and advantages thereof, may best be understood by reference to the following description taken in conjunction with the accompanying illustrative drawing.

BRIEF DESCRIPTION OF THE DRAWINGS

FIG. 2a is a schematic plan view of the embodiment of FIG. 1, in its undeployed configuration;

FIG. 2b is a schematic plan view similar to FIG. 2a, showing the embodiment of FIG. 1 in its deployed configuration;

FIG. 10A is a partial sectional view through the left shoulder of a human as seen from the front showing the use of a minimally invasive soft tissue to bone attachment system according to a presently preferred embodiment of the present invention;

FIG. 10B is an enlarged sectional view taken within the circle denoted 10B in FIG. 10A;

FIGS. 12A-12C are partial longitudinal sectional views through a distal end of an exemplary soft tissue to bone attachment system of the present invention;

FIG. 13A is a perspective view of a combined suture locking portion and bone anchor structure of the soft tissue to bone attachment system of the present invention, showing a locking plug disengaged from an anchor body;

FIG. 13B is a partial longitudinal sectional view of the combined suture locking portion and bone anchor structure taken along line 13B-13B of FIG. 13A;

FIG. 13C is an end elevational view of the combined suture locking portion and bone anchor structure taken along line 13C-13C of FIG. 13B;

FIG. 14 is a perspective view of an anchor body of the combined suture locking portion and bone anchor structure of FIG. 13A;

FIG. 15 is a top plan view of the combined suture locking portion and bone anchor structure without the locking plug and an attached actuation rod;

FIG. 16A is a perspective view of an exemplary suture locking portion of the soft tissue to bone attachment system of the present invention showing a locking plug disengaged from an anchor body;

FIG. 16B is a partial longitudinal sectional view of the suture locking portion taken along line 16B-16B of FIG. 16A;

FIG. 16C is an end elevational view of the suture locking portion taken along line 16C-16C of FIG. 16A;

FIG. 17A is a perspective view of the exemplary suture locking portion of the soft tissue to bone attachment system of the present invention showing the locking plug engaged with the anchor body;

FIG. 17B is a partial longitudinal sectional view taken along line 17B-17B of FIG. 17A;

FIG. 17C is an end elevational view taken along line 17C-17C of FIG. 17A illustrating the locking plug clamping a length of suture against an inner lumen of the anchor body;

FIG. 18A is a side elevational view of the deployed anchor structure relative to the anchor body and locking plug therein;

FIG. 18B is an end elevational view of FIG. 18A;

FIG. 19 is a partial sectional view through the left humeral head of a human as seen from the front showing the use of an alternative minimally invasive soft tissue to bone attachment system of the present invention;

FIG. 20A is a perspective view of a combined suture locking portion and bone anchor structure of the present invention, showing an alternative suture pulley structure; and FIG. 20B is a cross-sectional view taken along lines 20B-20B of FIG. 20A.

DESCRIPTION OF THE PREFERRED EMBODIMENT

Figure 1:
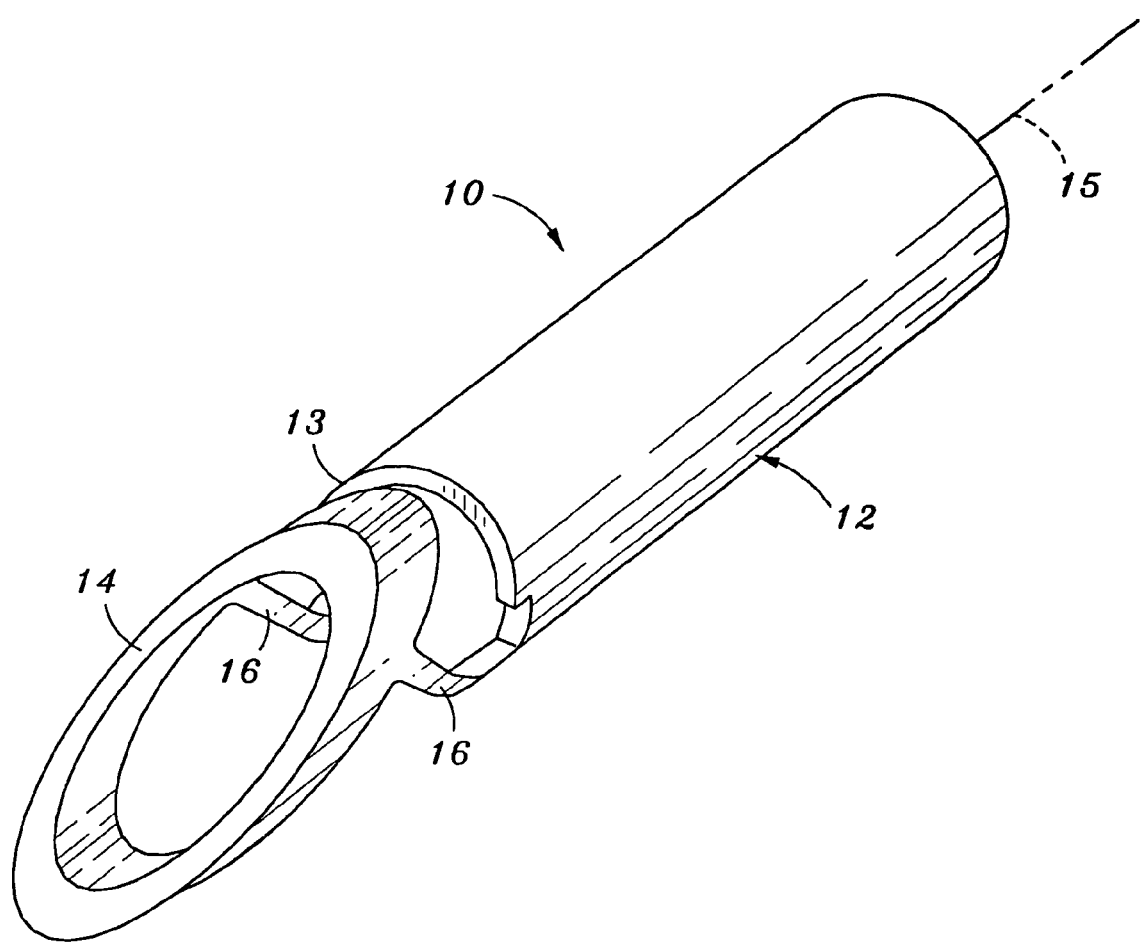
FIG. 1 is a perspective view of a first preferred embodiment of a bone anchor device constructed in accordance with the principles of the present invention.

Referring now more particularly to the drawings, there is shown in FIG. 1 a bone anchor 10, constructed in accordance with one embodiment of the present invention, in its undeployed state. The bone anchor 10 is preferably comprised of a tubular or cylindrical body 12, which may, for example, be a hypotube, in which a series of diagonal cuts have been made at its proximal end 13 to create an annular generally elliptical angled toggle ring member 14. The cuts may be made by using wire Electro-Discharge Machining (EDM) techniques, though many other suitable known methods and materials for fabricating a generally tubular body and associated proximal toggle ring member may be utilized as well. This toggle ring member 14 is generally oriented diagonally relative to a longitudinal axis 15 of the tubular anchor body 12. The toggle ring member 14 thus formed remains connected to the main portion of the tubular body 12 by two thin struts 16 which are situated such that they are substantially orthogonal to the orientation of the toggle ring member 14, and disposed at an acute angle θ relative to the longitudinal axis 15 (FIG. 2*a*).

It is preferred that the anchor 10 be fabricated of biocompatible materials such as 300-series stainless steel (Type 304 or Type 316, for example) or titanium, although suitable bioresorbable plastics may potentially be used as well.

Figure 3:
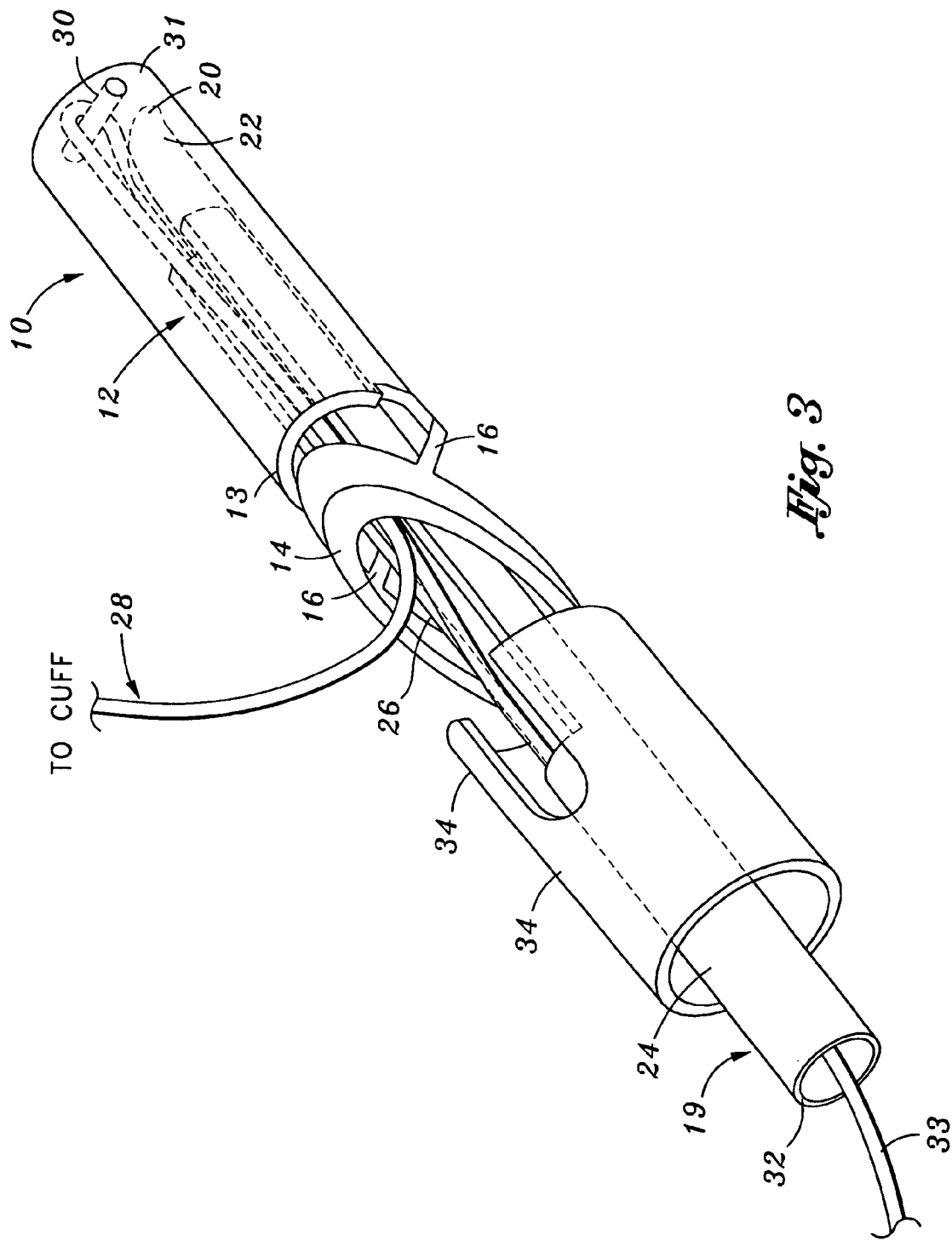
FIG. 3 is a perspective view of the bone anchor of FIG. 1, together with additional structure which is employed during installation of the bone anchor in a desired bone site.

FIGS. 2*a* and 2*b* are cross-sectional views of the bone anchor 10 in its undeployed and deployed states, respectively. FIG. 2*a* illustrates more clearly how the struts 16 connect the tubular body 12 to the toggle ring member 14. As can be seen in FIG. 2*b*, which illustrates the bone anchor in its deployed state, the struts 16 are designed so that they will readily bend or deform to an orientation which is substantially orthogonal (transverse) to the axis 15 when a force 17 is applied distally to the toggle ring member 14 and/or a force 18 is applied proximally to the tubular body 12. As the thin struts 16 bend responsive to the forces applied to the tubular body 12 and/or the toggle ring member 14, the toggle ring member is compressed against the tubular anchor body 12 until it is in a fully deployed transverse position relative to the anchor body 12 and the struts 16 are disposed in a relatively flat transverse orientation between the anchor body 12 and the deployed toggle ring member 14. The transverse orientation of the toggle ring member 14 relative to the anchor body 12 allows the toggle ring member 14 to present an effective anchoring profile to the cortical bone surface when the bone anchor apparatus 10 is deployed, as shall be more fully illustrated in the subsequent figures. Referring now to FIG. 3, a hollow casing 19 has been inserted into the bone anchor 10, and attached to the anchor body 12 utilizing methods well known in the art, such as crimping, welding or the like, in order to secure the bone anchor 10 to the casing 19. In the embodiment shown herein a substantially flat tongue 20 (see also FIG. 5) formed at the distal end of the casing 19, has been inserted into a slot 22 in the outer sidewall of the anchor body 12, and then welded at weldment 23 (FIG. 5) onto the outside surface of the anchor body 12. The casing 19 is attached to the bone anchor 10 to provide a means for inserting the bone anchor apparatus into the surgical area arthroscopically. The casing 19 is preferably of a hollow tubular shape at its proximal end 24 and preferably has a half-cylindrical shape at its distal end 26. This half cylindrical shape allows a length of suture 28 which has been threaded or stitched through desired soft tissue, such as a tendon, to be passed through the casing 19 and into the tubular body 12 through its open proximal end 13. The length of the suture 28 then preferably extends distally though the axial length of a lumen 29 of the body 12 and then around a suture return pin or pulley 30 at a distal end 31 of the body 12. The pin 30 may be fixedly secured within the body 12, or may alternatively be journaled to permit rotation. A further alternative approach is to secure the pin to the body 12 so that it may move axially. The suture returns through the lumen 29 in a proximal direction, exiting the body 12 from its proximal end 13 and then traversing the interior lumen of the hollow casing 19, exiting the hollow casing 19 from its proximal end 32 such that the free ends 33 of the suture 28 may be handled by the medical practitioner performing the subject procedure. Referring still to FIG. 3, in the illustrated embodiment, a hollow mandrel 34 is placed over the proximal end of the casing 19, in coaxial fashion, such that it may be moved in a distal direction until it comes into contact with the toggle ring member 14 connected to the proximal end of the body 12, thereby deploying such toggle ring member 14 as shall be shown in the following figures.

It should be noted, at this juncture, that, while a presently preferred means for securing the suture 28 to the bone anchor 10 has been illustrated, any other suitable means for securing suture to bone anchors known in the art may be utilized in combination with the inventive bone anchor 10. For example, the suture 28 may merely be knotted to a provided eyelet on the body 12, or through a suture receiving aperture or apertures on the anchor 10. Another alternative could be to wrap the suture about a portion of the anchor 10 to secure it thereto.

Figure 4:
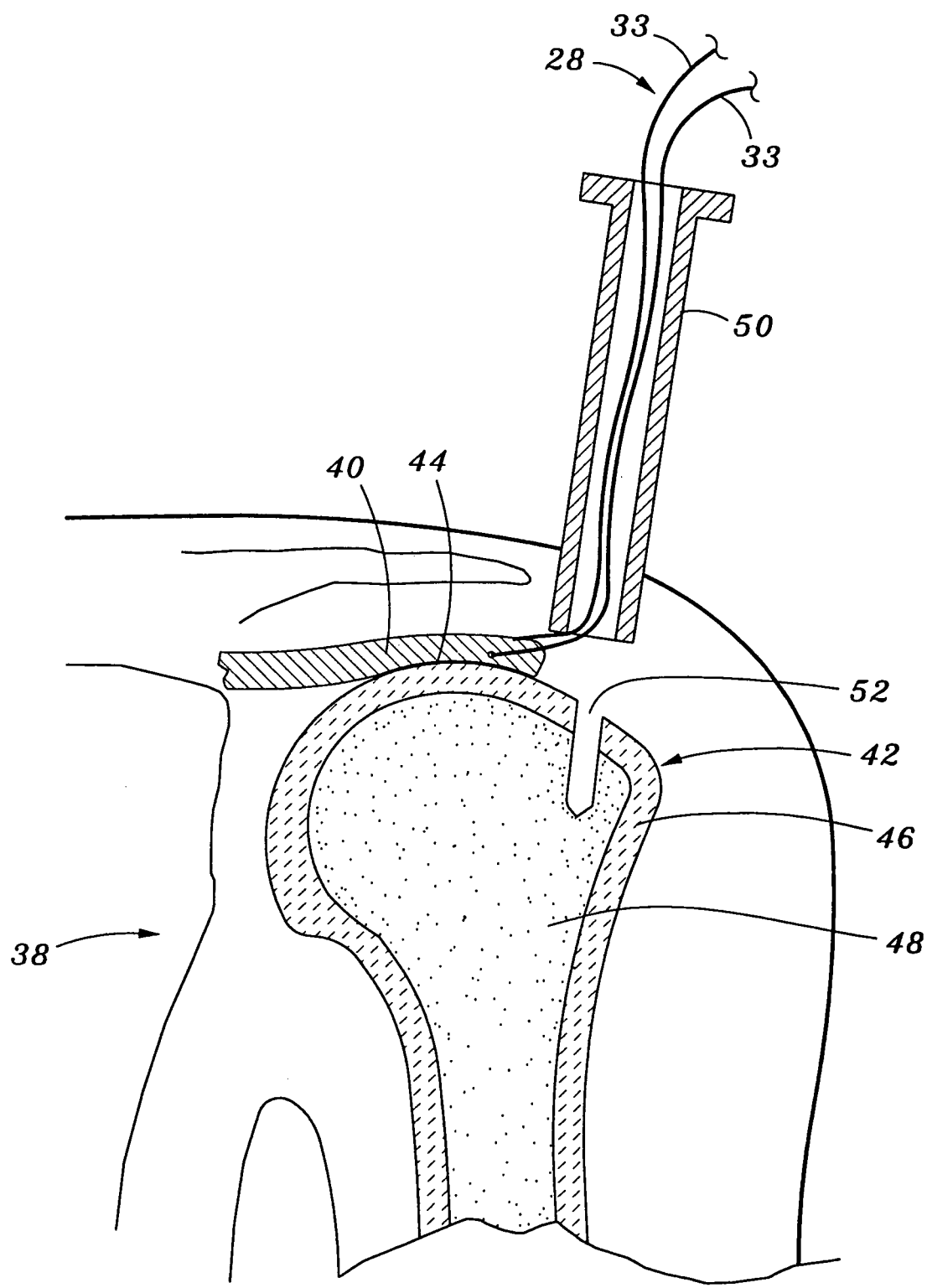
FIG. 4 is schematic cross-sectional view of a typical procedural site, in a human shoulder, for which the present invention may be employed.
Figure 5:
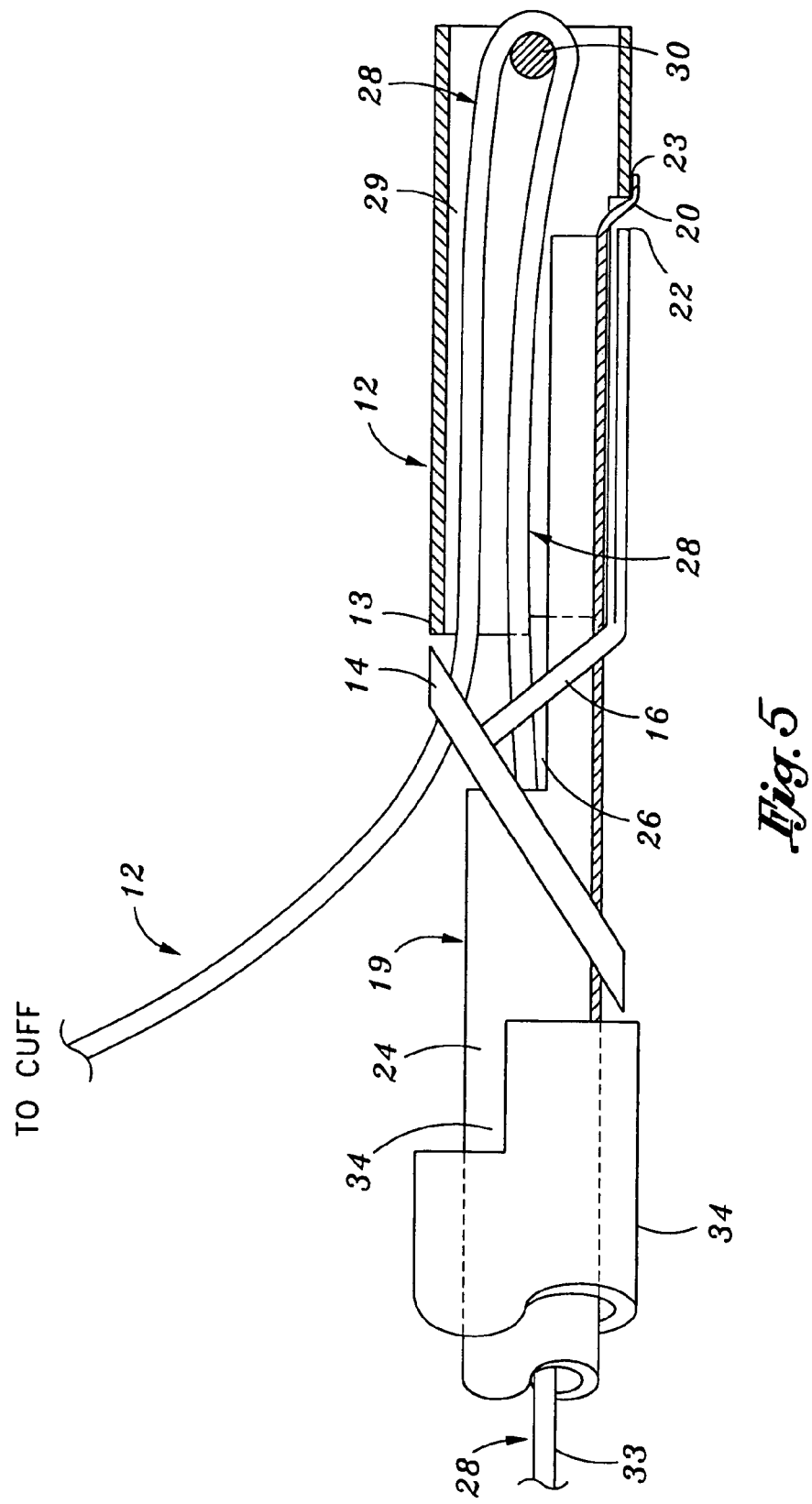
FIG. 5 is a plan view, partially in cross-section, of the embodiment illustrated in FIG. 3, wherein the anchor is in its undeployed configuration.
Figure 6:
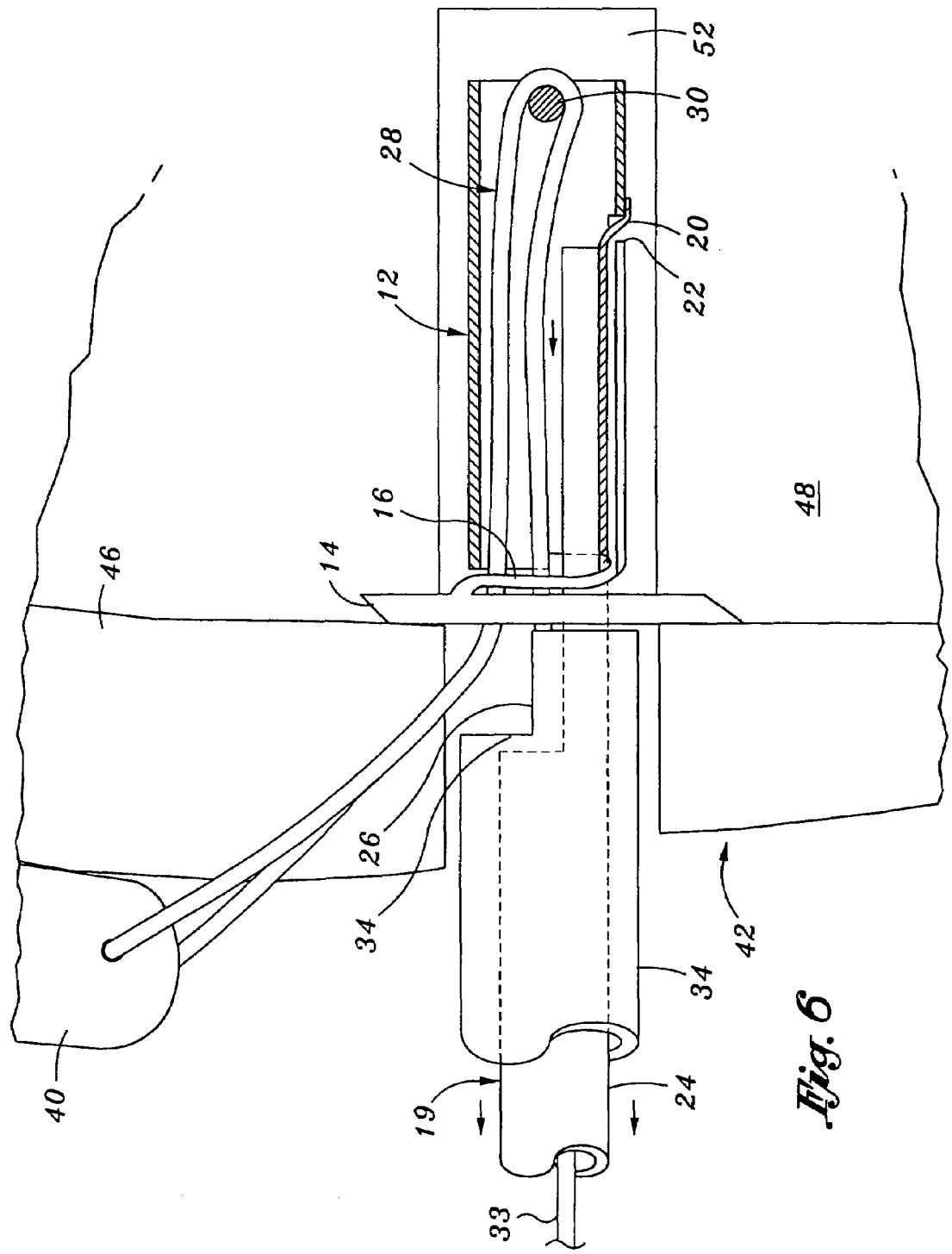
FIG. 6 is a plan view similar to FIG. 5, showing the anchor after it has been deployed.

Referring now in particular to FIGS. 4-6, the manner in which the bone anchor 10 is deployed into desired bone structure to secure soft tissue to bone will be described. In FIG. 4, there is shown a cross-sectional view of a human shoulder 38 on the left side of the body as seen from the front of the body and which illustrates a rotator cuff tendon 40 which is disposed across a humeral head 42. This illustration is intended only to provide a simple structural overview of the physiological elements involved in a typical situation involving the repair of a patient's rotator cuff, where it is to be desired that the rotator cuff tendon 40 be reattached to a humeral head 42. It should be noted, of course, that the invention is applicable to many other types of orthopedic repairs which involve the attachment of soft tissue to adjacent bone structure.

It is to be understood that, in this illustration, the rotator cuff tendon 40 is not attached to the humeral head 42 at the interface 44 between the two, as is typically the case when a patient's rotator cuff has become damaged due to injury or overuse, and requires repair. The humeral head 42 is comprised of an outer surface of cortical bone 46 and inner cancellous bone 48. A trocar 50 has been inserted into the shoulder 38 in proximity to the area where the rotator cuff tendon 40 is to be reattached to the humeral head 42, to allow for arthroscopic access, and a hole 52 has been made, preferably by drilling or punching, in the desired location through the cortical bone 46 and into the cancellous bone 48. A suture 28, is stitched in a suitable manner to the rotator cuff tendon 40 which is to be secured to the humeral head 42. The stitching process may be accomplished by any known means, and any known suture stitch may be employed, the objective being to ensure a secure stitch so that the suture is not inadvertently separated from the tendon after completion of the repair procedure, necessitating re-entry to the surgical site. In preferred approaches, the suture is attached to the soft tissue using a "mattress stitch", which is well known in the art as being a particularly secure stitch which is unlikely to fail postoperatively. Preferably, a suturing instrument is inserted into the trocar to perform the aforementioned suturing step. A preferred suturing approach is taught in co-pending application Ser. No. 09/668,055, entitled Linear Suturing Apparatus And Methods, filed on Sep. 21, 2000, expressly incorporated herein by reference and commonly assigned herewith. Of course, the inventive devices may also be utilized in an open surgical procedure, if desired, wherein the sutures are manually placed. Once the suturing process is completed, the free ends 33 of the suture 28 are removed proximally through the trocar from the patient's body, together with the suturing instrument.

As shown particularly in FIG. 5, the free ends 33 of the suture 28, while still outside of the patient's body, are then passed distally through the toggle ring member 14 and the casing 19, into the body 12, around the suture return pin 30, and then proximally out of the body 12 and casing 19 where the free ends 33 may be manipulated by the surgeon. In FIG. 5, the anchor apparatus 10 is still in its undeployed state. The mandrel 34 has been inserted over the casing 19 such that it is disposed adjacent to the proximal end of the toggle ring member 14 prior to deployment. In the presently preferred method, the entire apparatus 10, including the body 12, the casing 19, and the mandrel 34, once loaded with the suture 28, is then inserted through the trocar 50 and into the hole 52 in the humeral head 42 illustrated in FIG. 4.

FIG. 6 illustrates how the bone anchor is deployed after it has been inserted into the hole 52 in the humeral head 42. The entire apparatus is inserted into the hole 52 a sufficient distance so that the toggle ring member 14 is disposed just distally of the juncture between the cortical bone 46 and the cancellous bone 48, just within the cancellous bone 48. Once so positioned, the bone anchor 10 may be deployed within the cancellous bone 48 to lock the anchor 10 into position, thereby securely attaching the suture 28 to the humeral head 42. To deploy the anchor 10, in a preferred method, the casing 19 is withdrawn proximally. Because of its connection through joint formed between the tongue 20 and slot 22, this withdrawal force applied to the casing 19 will also cause the body 12 to move in a proximal direction until it engages the distal side of the toggle ring member 14. Preferably, the mandrel 34 is maintained in a stationary position, so that the continued proximal movement of the body 12 against the toggle ring member 14 results in the application of sufficient force on the struts 16 to cause them to deform, thereby decreasing the axial spacing between the toggle ring member 14 and the proximal end of the body 12 to a relatively small distance. Referring again to FIGS. 2a and 2b, this force applied against the toggle ring member 14 and struts 16 also cause the toggle ring member 14 to move in a pivoting fashion from an undeployed orientation, wherein the ring member 14 is disposed at an acute angle $\theta$ relative to the longitudinal axis 15 (FIG. 2a) to present a smaller profile in a direction transverse to the axis 15, to a deployed orientation, wherein the ring member 14 is disposed substantially transversely to the axis 15 (FIG. 2b) in order to present a larger profile in a direction transverse to the axis 15. This deployment of the toggle ring member and consequent increase in the transverse profile of the toggle ring member 14, causes the ends of the toggle ring member 14 to push or dig into the soft cancellous bone just beneath the surface of the cortical bone layer 46. Because the profile of the toggle ring member 14 in its deployed state is larger than the diameter of the hole 52, the apparatus is prevented from being pulled proximally out of the hole 52 after it has been deployed. The surface area of the toggle ring member 14 which is in contact with the cancellous bone 48 also prevents the apparatus from being moved either distally or laterally after deployment.

As noted supra, it is preferable to maintain the mandrel 34 in a stationary position, while moving the body 12 proximally to apply deployment force against the toggle ring member 14. The reason for this is that by holding the mandrel 34 steady, the practitioner can accurately control the depth at which the anchor 10 is deployed, so that the toggle ring member is deployed just distally of the distal surface of the cortical bone 46. If, instead, the mandrel were moved distally to apply force against the toggle ring member 14, ascertainment of the depth of the deployed toggle ring member would be more difficult. However, if desired, the mandrel 34 may be moved distally against the toggle ring member 14 while the casing 19 is maintained in a stationary position, thereby pushing the toggle ring member 14 distally until the resultant forces on the struts 16 cause them to deform. Still another alternative is to move the mandrel 34 distally, while at the same time moving the body 12 proximally, to apply both a proximally directed and a distally directed force against the toggle ring member 14 and associated struts 16.

Ideally, as noted supra, once the toggle ring member or arm 14 has been fully deployed, it will have rotated to an orientation fully transverse (90 degrees displaced from) the axis 15. In such an orientation, the future loads on the arm 14, caused by axial forces applied to the anchor 10 during usage of the shoulder (i.e. during rehabilitation therapy), will be columnar, and will thus not pose a substantial risk of cyclic loading on the arm, with its attendant risk of eventual failure. However, in actual cases, it is unlikely that the arm 14 will always be oriented at precisely a 90 degree angle to the axis 15, and it is therefore undoubtedly the case that the struts 16 will see some degree of cyclic rotational loading during the healing process. Thus, Applicants have determined that arm 14 and struts 16 should preferably be annealed during the manufacturing process, to soften the material from which they are formed, thereby making the struts more ductile, so that they can tolerate such loading without failing.

Figure 7:
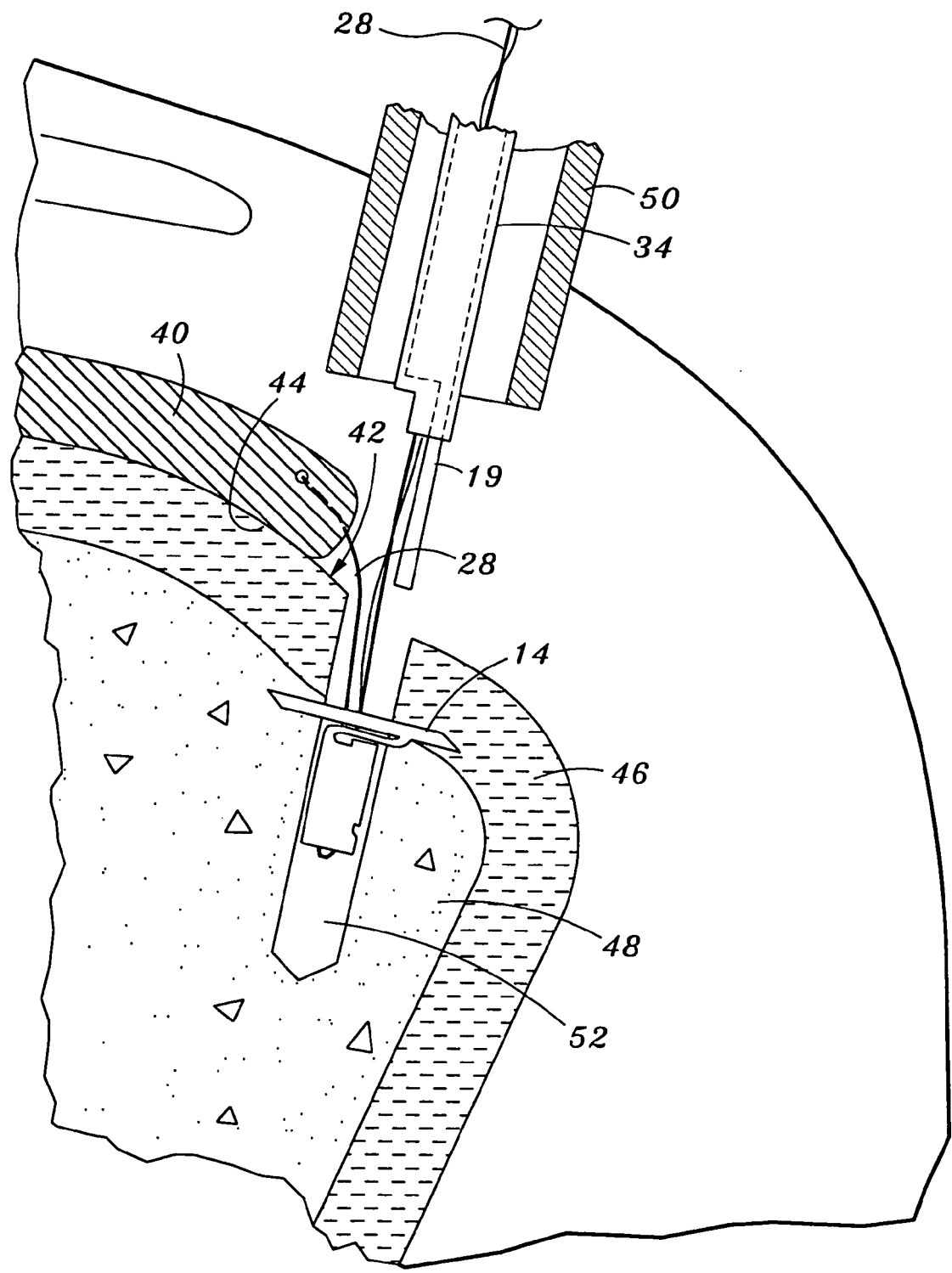
FIG. 7 is a cross-sectional view of a typical procedural site, illustrating a preferred method for closing the inventive repair procedure after the anchor has been deployed in a suitable bone site.

Referring still to FIG. 6, the manner in which the casing 19 and mandrel 34 are removed from the procedural site after deployment of the bone anchor 10 is illustrated. Once the toggle ring member 14 is firmly positioned in the cancellous bone 48 just below the cortical bone surface 46, the casing 19 is withdrawn in a proximal direction. The tongue 20 which is inserted through the slot 22 in the distal end 26 of the casing 19 is designed to break upon the application of a withdrawal force of a predetermined strength on the casing 19, which force is considerably less than the force necessary to pull the deployed bone anchor 10 out of the hole 52. As a result, the bone anchor 10 remains firmly in place while the casing 19 and the mandrel 34 are removed through the trocar and out of the body. FIG. 7 provides an overall view of the shoulder area and the bone anchor apparatus after the bone anchor 10 has been deployed into the hole 52 in the humeral head 42 and as the casing 19 and mandrel 34 are being removed through the trocar 50. After the casing 19 and mandrel 34 are removed from the procedural site, the free ends 33 of the suture 28 still extend through the trocar 50 and out of the body. The surgeon may then cinch and knot the free ends of the suture 28 to secure the suture 28 to the bone anchor 10, and to snug the tendon 40 to the humeral head 42, as desired, or may employ a separate suture-securing device. Many different methods or devices may be employed to attach the suture 28 to the bone anchor device 10 or to a separate suture securing device and these means will be well known to those of ordinary skill in the art. The precise means of securing the suture 28 is beyond the scope of this description.

Figure 8:
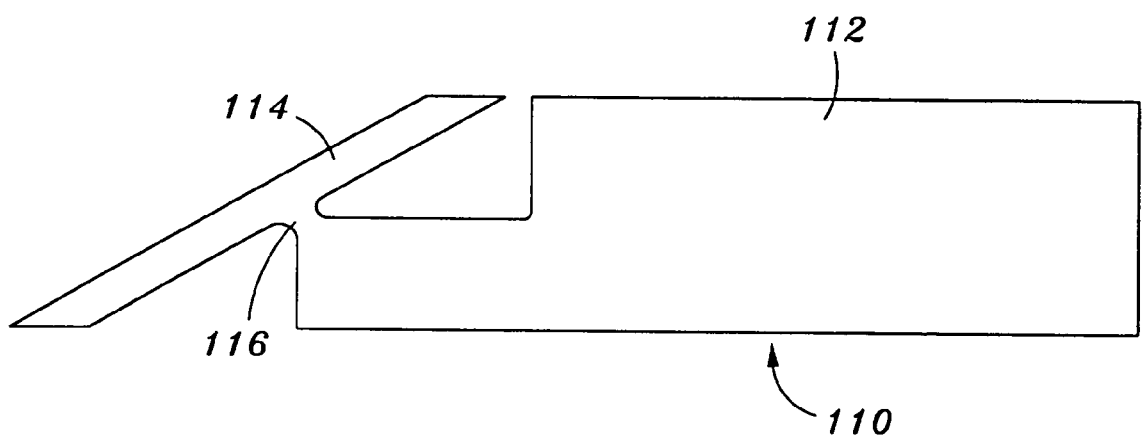
FIG. 8 is a schematic plan view of an alternative embodiment of the inventive bone anchor.

FIG. 8 illustrates an alternative embodiment of the present invention. A bone anchor 110 is shown which is similar to the bone anchor described in connection with the above illustrations. It comprises a tubular or cylindrical body 112 and a toggle ring member 114. The only significant difference in this alternative embodiment is the absence of the thin struts 16 shown in the prior figures. In this alternative embodiment the toggle ring member 114 is hinged directly to the anchor body 112. It is deployed in the same manner using a casing and a mandrel as described above, but in this embodiment the toggle ring member 114 simply bends at the hinge point 116 to move from its undeployed position (illustrated in FIG. 8) in relation to the anchor body 110 to its deployed position (not shown, but similar to the deployed position of the first embodiment illustrated in FIG. 2*b*).

Figure 9A:
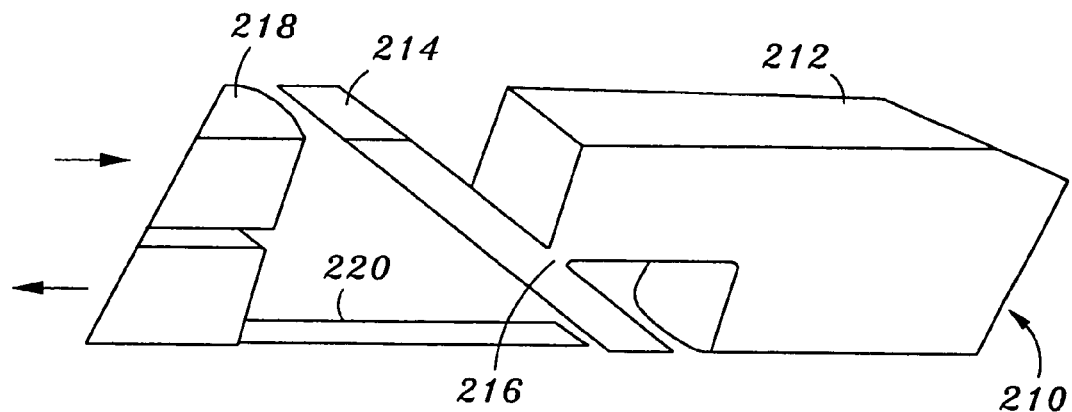
FIG. 9*a* is a perspective view of another alternative embodiment of the inventive bone anchor.
Figure 9B:
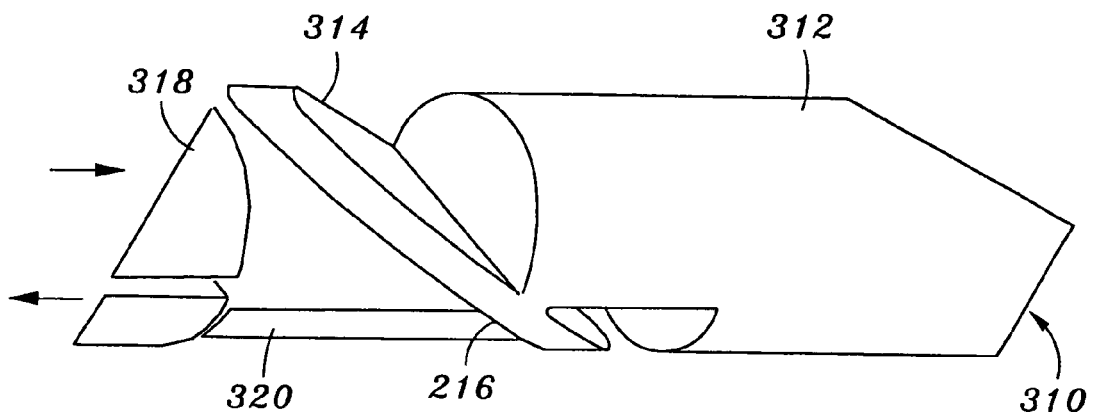
FIG. 9*b* is a perspective view, similar to FIG. 9*a*, of yet another alternative embodiment of the inventive bone anchor.
Figure 9C:
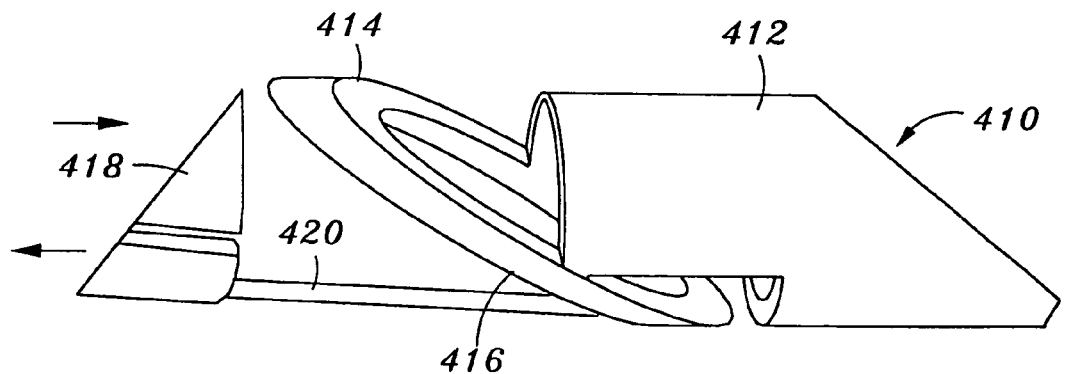
FIG. 9*c* is a perspective view, similar to those of FIGS. 9*a* and 9*b*, of still another alternative embodiment of the inventive bone anchor.

Additional alternative embodiments of the present invention may be seen by referring to FIGS. 9*a*-*c*. FIG. 9*a* shows an embodiment consisting of a substantially rectangular anchor 210 having a solid anchor body 212 and a solid rectangular member 214 attached by means of a hinge 216 for deployment into the bone structure below the cortical surface. Rather than using a casing that is inserted into the anchor body as in the embodiments described above, the rectangular member 214 is deployed by means of a mandrel 218 which pushes a first end of the rectangular member 214 distally at the same time that a rod 220 attached to the opposing end of the rectangular member 214 pulls that end proximally, thereby deploying the member 214 to an orientation having a greater transverse profile, as in the prior embodiments. The rod 220 is designed such that it will break away from the rectangular member 214 when a proximal force is exerted on it after deployment of the rectangular member 214 so that the rod 220 and the mandrel may be removed.

The alternative embodiment shown in FIG. 9*b* is deployed in exactly the same manner as the embodiment shown in FIG. 9*a*. The only difference between the two embodiments is the configuration of the anchor 310, which has a tubular body 312 and a tubular toggle ring deployment member 314.

FIG. 9*c* shows yet another alternative embodiment of a bone anchor 410 with a hollow tubular body 412, and a hollow toggle ring deployment member 414 similar to the embodiment described above, supra, but which is deployed by means of a mandrel 418 and rod 420 as with the alternative embodiments described in connection with FIGS. 9*a* and 9*b*.

In FIGS. 10A through 20B are illustrated a preferred embodiment which includes a presently preferred suture anchoring approach. FIGS. 10-10B and 11A-11D are cross-sectional views through the left shoulder of a human as viewed from the front and illustrate the use of an exemplary suture anchor system 520 for repairing a rotator cuff tendon injury. The rotator cuff tendon 522 is shown in its natural positioned overlying the bulbous humeral head 524 of the humerus bone 526. In rotator cuff injuries, the tendon 522 partially or completely separates from its attachment point to the humeral head 524, which point of attachment is typically located along an angled shelf, the greater tuberosity 528. In minimally invasive surgeries to repair the rotator cuff injury, the surgeon threads one or more sutures through the rotator cuff tendon 522 and anchors them to the greater tuberosity 528. The suture anchor system 520 of the present invention facilitates this latter step of anchoring the sutures to the greater tuberosity 528.

With reference first to FIG. 10A, a generally tubular trocar 530 provides a conduit through the soft tissue of the shoulder for the suture anchor system 520 of the present invention. Typically, the surgeon makes an incision or stab wound through the outer dermal layers of sufficient size to permit passage of the trocar 530 through skin and the deltoid muscle into proximity with the humeral head 524. Various trocars and techniques for creating the approach passageway are known and may be utilized with the present invention. In addition, more than one incision and conduit may be necessary to perform the several suturing and anchoring steps.

After establishing one or more direct conduits to the humeral head 524, the surgeon passes a length of suture through the soft tissue of the rotator cuff tendon 522 so that a loop 532 of suture material is embedded therein, as seen in FIG. 10B. The two free ends 534a, 534b of the length of suture are withdrawn from the patient and coupled to the suture anchor system 520. The specifics of this coupling and subsequent manipulation of the two free ends of the suture will be described more fully below. For the purpose of explaining the exemplary method of use, it is sufficient to understand that the two free ends 534a, 534b pass into a lumen at the distal end of the suture anchor system 520 and extend through the lumen in a proximal direction to a proximal end of the system to enable fixation or pulling of the suture ends. As seen in FIG. 10B, the two free ends 534a, 534b are shown projecting from a proximal end of the system. The system 520 further includes a plurality of concentrically disposed cannulas or tubes as shown that perform the knotless suture anchoring operation. The interrelationship and functioning of these tubes will also be more fully explained below.

The exemplary system 520 as illustrated is particularly suitable for anchoring a suture to a body cavity, specifically the humeral head 524 as shown. When anchoring sutures to such a bone structure, a conventional technique is to first form a blind hole or cavity 540 through the cortical layer 542 and into the soft cancellous matter 544, as seen in FIGS. 10A-10B and 11A-11D. The surgeon then positions a suture anchor 546 within the cavity 540 and deploys it such that it cannot be removed from the cavity.

The suture anchor 546 performs two functions: anchoring itself within the body cavity and anchoring the sutures therein. In the illustrated embodiment, the former function is accomplished using an expandable anchoring structure 548 located on the proximal end of the suture anchor 546. The anchoring structure 548 is preferably the toggle ring 14 illustrated in FIGS. 1-7, and functions like a toggle bolt used in ceiling fixtures, specifically expanding to a larger dimension in the cavity 540 beyond the hard cortical bone 542. In this manner, the suture anchor 546 is prevented from being removed from the cavity 540 once the anchoring structure 548 is deployed. Although the present invention illustrates a particular anchoring structure 548, which is similar to the afore-described toggle ring 14, it should be noted that any similar expedient will work. For example, a different toggle-like anchoring structure may be used such as shown in co-pending application Ser. No. 09/616,802, filed Jul. 14, 2000, the disclosure of which is hereby expressly incorporated by reference. Alternatively, an anchoring structure that expands into contact with the cancellous matter 544 may be used.

Figure 11B:
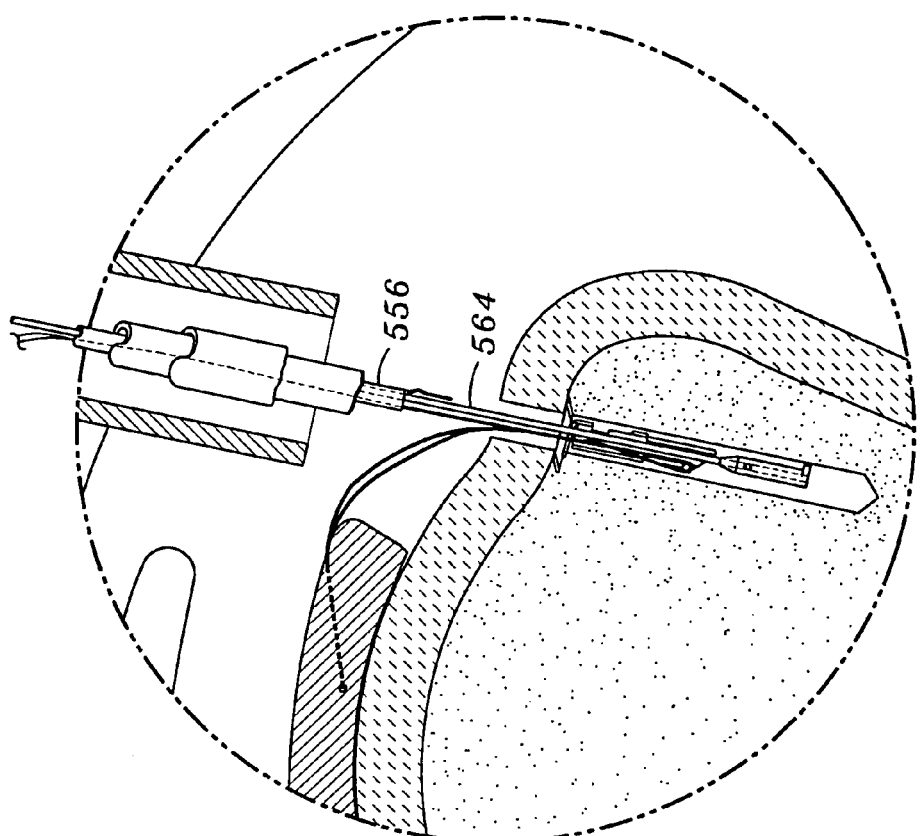
FIGS. 11A-11D are enlarged sectional views of the use of the soft tissue to bone attachment system of FIG. 10A to reattach a rotator cuff tendon.
Figure 11A:
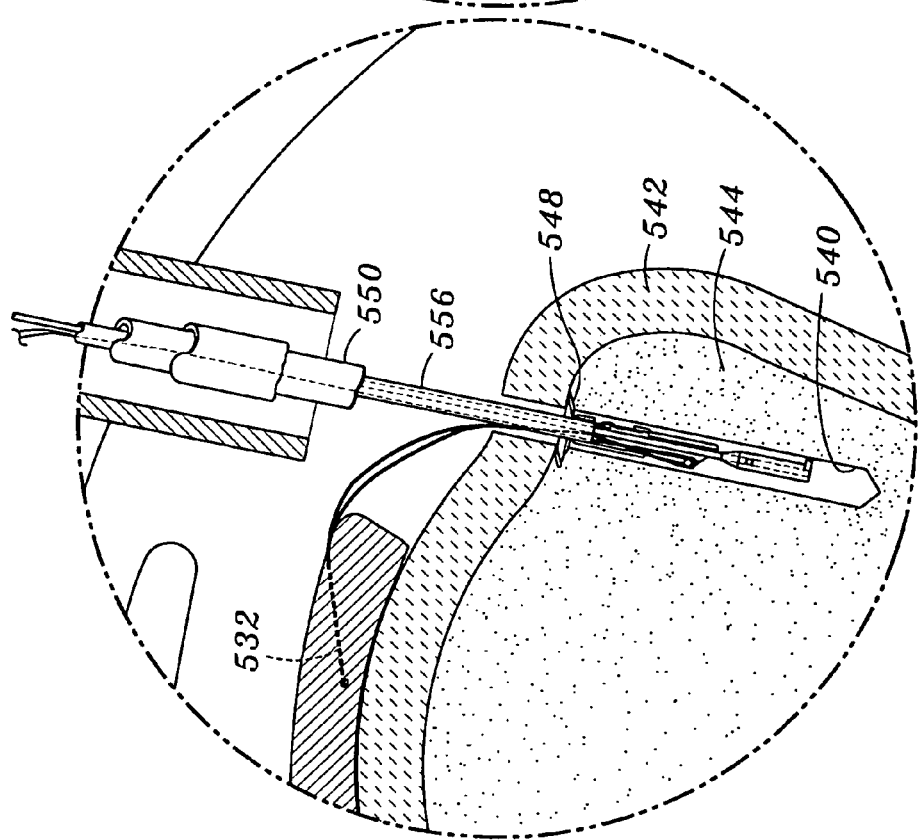

The second function of the suture anchor 546 is the anchoring or fixation of the suture with respect to the suture anchor itself, without the use of knots. Desirably, the particular manner of anchoring the suture with respect to the suture anchor 546 permits easy adjustment of the length of suture between the suture anchor and the loop 532 formed in the soft tissue. This adjustment allows the surgeon to establish the proper tension in the length of suture for effective repair of the soft tissue; reattachment of the rotator cuff tendon 522 in the illustrated embodiment. In this regard, FIG. 11D shows the fully deployed suture anchor 546 after the free ends 534a, 534b have been placed in tension and locked within the suture anchor. Although not shown, the remaining steps in the procedure involve withdrawing the concentric tubes from the surgical site and severing the free ends 534a, 534b close to the suture anchor 546.

Figure 12A:
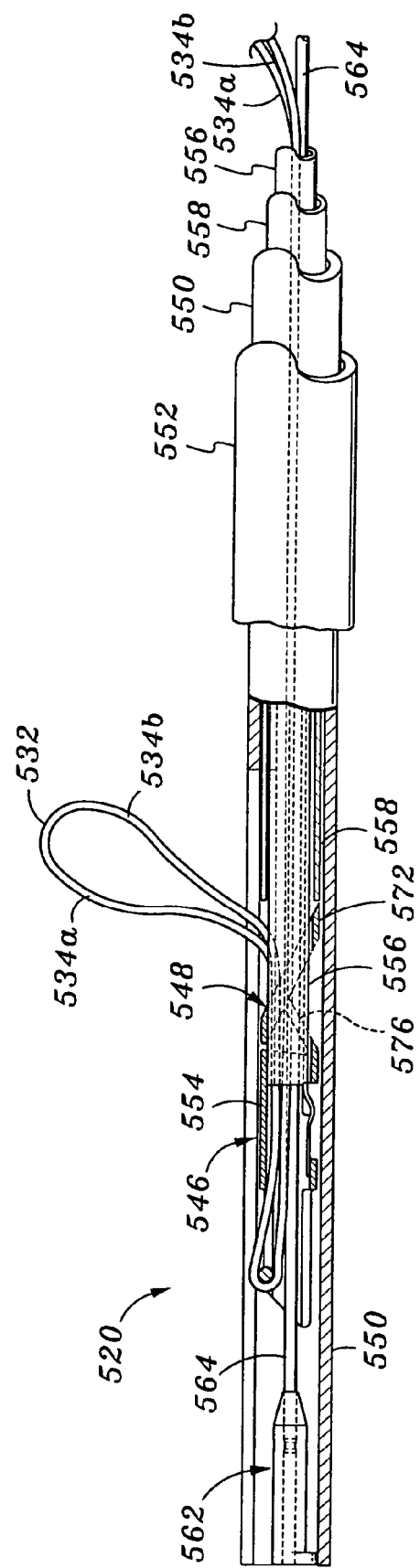

FIGS. 12A-12C are different partial longitudinal sectional views taken through the exemplary suture anchor system 520 of the present invention. The suture anchor 546 is seen in cross-section disposed in a close-fitting relationship within a delivery tube 550. The delivery tube 550, in turn, may be arranged to slide within a larger tube 552, sometimes known as an introducer tube, that includes a valve (not shown) on a proximal end to prevent fluid leakage therefrom. Alternatively, such a fluid leakage valve may be provided on the proximal end of the trocar 530 seen in FIGS. 10A-10B.

The suture anchor 546 is defined by a generally tubular anchor body 554 and an inner deployment tube 556 fits closely within a proximal end and is fastened therein. The exemplary suture anchor 546 is shown and described in greater detail below with respect to FIGS. 13A-14. The deployment tube 556 can also be seen on the right side in FIG. 12A projecting from the series of concentric tubes, with the free ends 534a, 534b of the length of suture projecting therefrom. A die tube 558 sized intermediate the delivery tube 550 and the deployment tube 556 is arranged for longitudinal displacement over the deployment tube 556. In the illustrated state of the system 520, the suture anchor 546 is undeployed within the delivery tube 550 and the die tube 558 is positioned just proximal to the expandable anchoring structure 548. A further component of the suture anchor system 520 is a suture locking plug 562 having an actuation rod 564 removably attached to a proximal end thereof and extending proximally within the deployment tube 556.

FIGS. 12A-12C all show the suture loop 532 extending transversely from within the concentric tubes of the suture anchor system 520. In this regard, the delivery tube 550 is provided with an axial slot 565, the deployment tube 556 is provided with an axial slot 566, and the die tube 558 has an axial slot 567. The free ends 534a, 534b of the length of suture pass through these aligned axial slots 565, 566, 567 to the interior of the deployment tube 556 that opens into the lumen 568 of the tubular body 554. The aligned axial slots 565, 566, 567 permit passage of the free ends 534a, 534b into the system 520 from a location midway along the concentric tubes, as indicated in FIGS. 10A-11D.

The various described components of the suture anchor system 520 are relatively axially movable to deploy the suture anchor 546. Various means are known to relatively displace concentric tubes a predetermined distance and/or with a predetermined displacement force. For example, the concentric tubes may extend out of the trocar 530 to an actuation device in the form of concentric syringe bodies/finger tabs. Alternatively, the concentric tubes may be attached to relatively movable parts in a gun-type handle, and actuated by triggers or other such levers. It is to be understood therefore that the present invention is not limited by the particular actuation device on its proximal end, and no further description in this regard will be provided.

A more complete understanding of the exemplary suture anchor 546 will be helpful prior to a detailed description of the structure and function of the concentric tubes to deploy the system. In this regard, FIGS. 13A-15 illustrate one embodiment of a suture anchor 546 isolated from the remainder of the system and having the aforementioned tubular anchor body 554 and deployable anchoring structure 548.

The anchor body 554 defines a lumen 568 therewithin. FIGS. 13A and 13B also illustrate the suture locking plug 562 and attached actuation rod 564.

The anchor body 554 has the anchoring structure 548 on its proximal end and a suture pulley or suture return member 570 disposed in proximity to its distal end. The aforementioned suture loop 532 is schematically illustrated out of the soft tissue for clarity, and it should be understood that this suture loop 532 is embedded in the soft tissue in actual use of the system. The free ends 534a, 534b of the length of suture pass through an angled toggle ring 572 of the anchoring structure 548 and into an open proximal end 574 of the lumen 568 formed within the tubular anchor body 554. The angled toggle ring 572 attaches to the proximal end 574 via a pair of plastically deformable struts 576. Both the toggle ring 572 and struts 576 are initially formed as a projection of the tubular anchor body 554. After continuing in the distal direction through the lumen of the anchor body 554, the free ends 534a, 534b wrap around the suture return member 570 and traverse the lumen in the proximal direction to emerge from the angled toggle ring 572 as shown.

As best seen in FIG. 13B, the actuation rod 564 extends into an open distal mouth 576 of the anchor body 554 and through the lumen 568 and angled toggle ring 572. The actuation rod 564 and four strands of the length of suture thus share the space within the lumen 568. Because of the relatively smaller size of the actuation rod 564 with respect to the lumen 568, the length of suture may slide axially within the lumen without interference. It can therefore be seen that because the suture loop 532 is embedded in soft tissue, pulling on the free ends 534, 534b of the length of suture places the suture loop in tension.

Prior to a more exhaustive description of the function of the locking plug 562 to perform the second function of the suture anchor 546 (i.e., anchoring the length of suture with respect to the suture body 554), use of the concentric tubes to deploy the anchoring structure 548 will be explained. With reference again to FIGS. 12A-12C, the deployment tube 556 can be seen attached within the lumen 568 of the anchor body 554 using a tab 580. Of course, other means for attaching the deployment tube 556 within the lumen of a body 554 may be provided, but a small tab 580 bent inwardly from the anchor body 554 and welded or otherwise secured to the deployment tube 556 is a suitable expedient. The tab 580 is desirably provided at only one location around the circumferential junction between the deployment tube 556 and lumen 568 to facilitate severing of this connection, although more than one attachment may be provided. The tab 580 thus secures the deployment tube 556 within the anchor body 554 of the suture anchor 546, while both the die tube 558 and actuation rod 564 can freely slide with respect to the anchor body 554.

After positioning the delivery tube 550 in proximity with the preformed body cavity 540 as seen in FIGS. 10A and 10B, the surgeon advances the deployment tube 556 having the suture anchor 546 attached thereto into the cavity. The suture locking plug 562 and die tube 558 advance along with the deployment tube 556, and the resulting configuration is seen in FIG. 10B.

Using a depth measurement, or visualization technique, the surgeon insures that the suture anchor 546, and in particular the anchoring structure 548, has been inserted past the hard outer layer of cortical bone 542. The anchoring structure is then expanded as seen in FIG. 11A. To accomplish this, the die tube 558 contacts the angled toggle ring 572 and forces it into an orientation that is generally perpendicular with respect to the axis of the suture anchor 546. With reference to FIGS. 12A-12C, the die tube 558 is desirably held stationary while the deployment tube 556 having the suture anchor 546 attached thereto is pulled in a proximal direction. Again, the relative movement of these tubes can be accomplished using a handle or other device exterior to the patient's body. Pulling on the deployment tube 556 forces one side of the angled toggle ring 572 against the generally circular distal mouth of the deployment tube 556 which deforms the struts 576 as the toggle ring 572 moves into a perpendicular orientation.

After the anchoring structure 548 is deployed, further pulling on the deployment tube 556 detaches it from the suture anchor 546. Specifically, the aforementioned welded tab 580 severs at a predetermined pulling force. The die tube 558 remains in place in its fixed position, and provides a reaction force against the suture anchor 546. The deployment tube 556 is then pulled free and retracted out of the way, as indicated in FIG. 11B. At this stage, the suture anchor 546 is secured with respect to the body cavity, but the length of suture passing therethrough remains free to be axially displaced.

Now with specific reference to FIGS. 12A-12C, the path of the length of suture through the suture anchor system 520 will be described. The suture loop 532 is seen projecting upward from the system, but it again should be noted that this loop is embedded in soft tissue in use of the system. The two free ends 534a, 534b extend through an axial slot 590 in the delivery tube 550, and through an axial slot 590 in the deployment tube 556 into lumen 568 of the suture can 546. As best seen in FIG. 12C, the free ends pass through the lumen 568 and around the aforementioned suture return member 570. The free ends then travel in a proximal direction through the lumen 568 and through the lumen of the deployment tube 556 to emerge from proximal end of the system. Because the suture loop 532 is embedded in soft tissue, pulling on both of the free ends 534a, 534b, or pulling on one end while holding one fixed, will create tension in the length of suture. The suture return member 570 provides relatively little resistance to sliding of the length of suture therearound, and thus this tensioning can be accomplished relatively easily.

In one embodiment, the suture return member 570 comprises a pin oriented transversely to the axis of the suture anchor 546 and located along a sidewall thereof. As seen best in FIG. 13A, the pin may span an axial slot 600 in a sidewall of the anchor body 554 so that the free ends 534a, 534b of length of suture can pass out through the slot and around the pin. Alternatively, two axially spaced holes with chamfered or rounded edges may be formed in the sidewall of the anchor body 554 through which the free ends 534a, 534b can be threaded and fixed. Of course, numerous structures are contemplated that provide the function of the illustrated pin-type suture return member 570. Moreover, instead of being a fixed structure, the suture return member 570 can be arranged to swivel or otherwise move to facilitate sliding motion of the free ends 534a, 534b therearound. In a specific example, the pin-type suture return member 570 can be formed separately from the anchor body 554 and inserted within a pair of facing holes in the edges of the slot 600. In this manner, the pin-type suture return member 570 rotates within the holes, thus reducing friction between the free ends 534a, 534b and the suture return member.

Figure 11C:
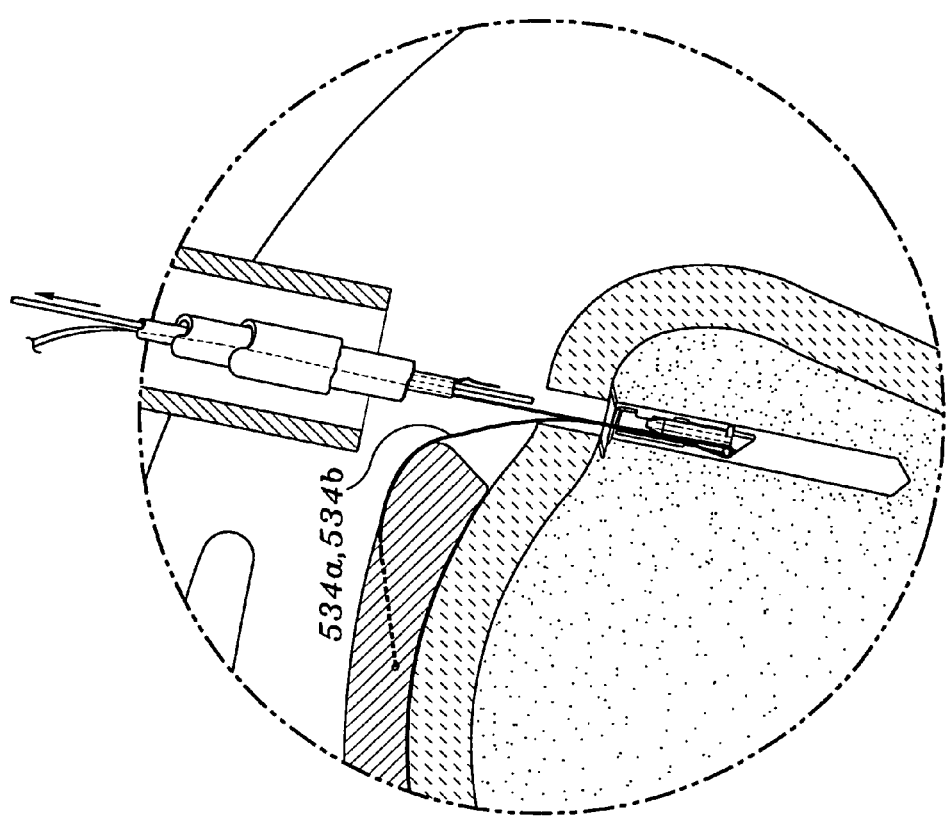
Figure 11D:
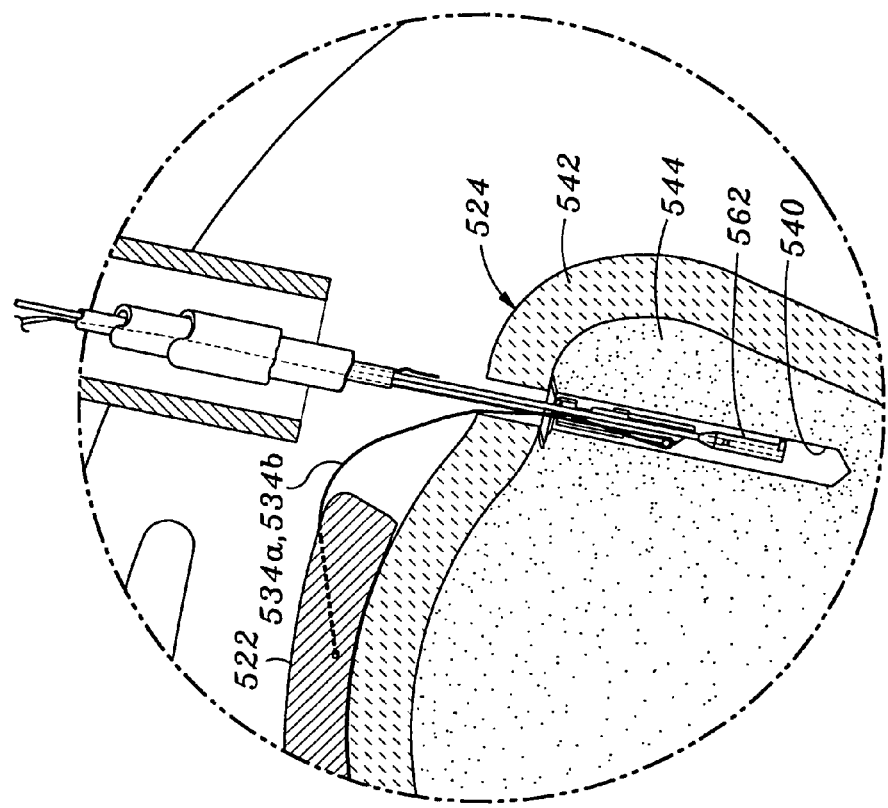

The step of tensioning the length of suture is seen in FIG. 11C, wherein the suture locking plug 562 remains in its initial position spaced from the anchor body 554. Adjustment of the length of the suture between the suture anchor 546 and the loop 532 is very important to ensure proper fixation of the rotator cuff tendon 522 with respect to the humeral head 524. If the suture is pulled too tightly, the rotator cuff tendon 522 may be unduly stressed, and the loop 532 may even pulled free from the tendon. On the other hand, if the suture is too loose, the goal of reattaching the tendon 522 in its proper location will be compromised.

Once the surgeon has established proper tension on the suture, the suture is anchored with suspect to the anchor body 554. This is done by displacing the suture locking plug 562 in a proximal direction so that it is forced into the lumen 568. The plug 562 includes a generally cylindrical shaft 602 with a bullet-shaped proximal nose 604 to help prevent its catching on a distal mouth 605 of the anchor body 54. Proximal displacement of the actuation rod 564 from outside the body causes proximal movement of the attached plug 562.

FIGS. 16A-17C show the anchor body 554 without the aforementioned anchoring structure 548, for clarity. These views illustrate the movement of the suture locking plug 562 into the lumen 566, and consequent locking of the length of suture therein. The diameter of the cylindrical shaft 602 of the plug 562 is sized to be slightly smaller than the inner diameter of the lumen 568. As seen in FIGS. 17B and 17C, the diameter of the cylindrical shaft 602 is such that it compresses the four strands of the length of suture against the lumen 568. The locking plug 562 is dimensioned to compress or "crush" the length of suture in the lumen 568 and interfere with its axial movement therethrough. The amount of compression may be measured by the amount of pull force on the suture necessary to move it once the plug is in position. Desirably, the pull force is in a range that would exceed the USP (United States Pharmacopeia) Standard knot pull strength (USP 24) of the suture used. In the specific case of #2 braided polyester suture, this knot pull strength is approximately 3.5 Kgf. In practice, however, the knot pull strength of commercially available #2 braided polyester sutures approaches 14 Kgf.

Proximal displacement of the locking plug 562 within the anchor body 554 is desirably limited by a positive stop. In the illustrated embodiment, a stop flange 610 projects outwardly from the cylindrical shaft 602 at its distal end. The stop flange 610 slides within an axial slot 612 at the distal end of the anchor body 554 that terminates at a slot end 614. Although not shown in the figures, proximal movement of the locking plug 562 is ultimately restricted by contact between the stop flange 610 and the slot end 614. Of course, other configurations that provide a positive stop to proximal movement of the locking plug 562 are contemplated. For example, rather than dimensioning the locking plug 562 to be larger than the lumen 568 of the anchor body 554 (as exhibited by the stop flange 610), a stop surface may project inwardly from the lumen 568 to interfere with movement of the plug 562.

One advantage provided by the present invention is the ability to tighten a suture loop embedded within soft tissue to a predetermined tension, and then locked to the suture within a suture anchor without even slightly altering that tension. As best seen in FIG. 17B, the locking plug 562 is shown partly inserted within the tubular body 554 during the step of being pulled proximal by the actuation rod 564 as indicated by the movement arrows 616. The free ends 534a, 534b of the length of suture extend around the suture return member 570, having previously been tensioned to a predetermined amount. Proximal movement of the locking plug 562 acts on all four strands of the length of suture within the lumen of the tubular body 554, and thus imparts equal frictional forces to all of the strands tending to urge them in a proximal direction. Because the four strands loop around the suture return member 570, with two coming and two going, these frictional forces cancel out such that the free ends 534a, 534b do not migrate within the tubular body 554. Because the suture return member 570 and tubular body 554 remain fixed with respect to the suture loop 532 (which is embedded within the soft tissue), the predetermined tension within the loop remains constant during the suture locking step.

In a further example, as seen in FIGS. 18A and 18B, deformation of the angled toggle ring 572 forces it into an oval shape at the proximal end 574 of the anchor body 554. This oval shape may have a minor dimension that is smaller than the diameter of the cylindrical shaft 602, or more typically the struts 576 may be bent into the path of the shaft 602, thus presenting an interference and a positive stop to the shaft movement. Alternatively, the actuation rod 564 may be bent back upon the exterior surface of the locking plug 562 to form the stop surface.

Once the suture locking plug 562 has been positively stopped, the actuation rod 564 may be detached therefrom. As seen in the figures, the actuation rod 564 extends within a through bore in the cylindrical shaft 602 and includes a frangible point 620 in that bore. The segment of the actuation rod distal to this frangible point 620 is secured within the bore in a conventional manner, such as with crimping indicated at 622 in FIG. 16A. The die tube 558 may be used as a reaction force against the anchor body 554 while the actuation rod 564 is pulled in the proximal direction, causing the frangible point 620 to fracture. The final configuration is seen in FIG. 11D.

As mentioned above, the exemplary structure for locking sutures relative to a body cavity may be utilized in a variety of anatomical environments. For instance, FIG. 19 shows an alternative surgical technique for using a combined suture anchor 546' and anchoring structure 548' to repair a rotator cuff tendon 522. In this embodiment, rather than forming a blind cavity within the humeral head 524, the surgeon forms a cavity 630 that transects the greater tuberosity 528 and opens through the cortical layer 542 at both ends. After embedding the loop 532 of suture material within the rotator cuff tendon 522, the free ends 534a, 534b are inserted into and threaded through the cavity 630. The ends 534a, 534b are then passed through the lumen formed within the combined suture anchor 546' and anchoring structure 548', which combination is then inserted as shown into the cavity 630. The free ends 534a, 534b of suture are then tightened to the prescribed level and secured within the suture anchor 546'. It should be noted that the combined suture anchor 546' and anchoring structure 548' may be configured somewhat differently to permit the aforementioned tightening step, though the suture locking steps are preferably accomplished in the same manner as described above; namely, with a suture locking plug compressing the length of suture within the suture anchor 546'. Furthermore, the anchoring structure 548' contacts the exterior of the cortical bone rather than the interior as described above.

FIGS. 20A and 20B illustrate an alternative suture anchor 640 of the present invention having a body cavity anchoring structure 642 on a proximal end. A length of suture is shown having a loop 644 and a pair of free ends 646a, 646b passing through the anchoring structure 642 and through a lumen 648 of a generally tubular body 650 of the suture anchor 640. In a distal portion of the tubular body 650, the free ends 646a, 646b pass out of the lumen 648 through a first aperture 652a and re-enter the lumen through a second aperture 652b located distally from the first aperture. As illustrated, the lumen 648 in the region of the apertures 652a, 652b is only partly defined by a semi-cylindrical extension of the tubular body 650, but other arrangements having a more complete lumen at this location are within the scope of the present invention.

With reference to FIG. 20B, the apertures 652a, 652b are shown to be rounded to reduce abrasion on the suture free ends 646a, 646b. In addition, the bridge portion 654 of the tubular body 650 that separates the apertures 652a, 652b defines a suture return member structure, much like the suture return member 570 (FIG. 17B) described above in the earlier embodiment. That is, the suture free ends 646a, 646b can easily slide with respect to the bridge portion 654, especially because of the rounded corners, to permit tightening of the suture loop 644 prior to locking the length of suture within the tubular body 650. The length of suture may be locked within the tubular body 650 using a locking plug as described above, or with another similar expedient.

It is to be understood that the figures of the bone and anchors seen above are purely illustrative in nature, and are not intended to perfectly reproduce the physiologic and anatomic nature of the humeral head as expected to be seen in the human species, nor to limit the application of the inventive embodiments to repair of the rotator cuff. The invention is applicable to many different types of procedures involving, in particular, the attachment of connective or soft tissue to bone. All of the terms used herein are descriptive rather than limiting, and many changes, modifications, and substitutions may be made by one having ordinary skill in the art without departing from the spirit and scope of the invention, which is to be limited only in accordance with the following claims.

What is claimed is:

1. A method of using suture to secure soft tissue with respect to a body cavity, comprising:
    passing a length of suture material through soft tissue so that a loop of suture material is disposed in the soft tissue, resulting in two free ends;
    passing the two free ends of the length of suture distally through an aperture in an anchoring structure and into a longitudinally disposed lumen of an anchor body through an open proximal end of the lumen, the open proximal end disposed distally of the anchoring structure, and looping the two free ends about a suture return member disposed in the anchor body such that the two free ends of the suture extend proximally from the lumen through said open proximal end and the aperture, the anchor body having a longitudinal axis extending from the proximal end to a distal end, said lumen extending along said longitudinal axis;
    inserting the anchor body and the anchoring structure into the body cavity;
    fixing the anchor body with respect to the body cavity wherein said step of inserting is separate from the step of fixing, and wherein the step of fixing comprises deforming a connecting portion between the anchor body and the anchoring structure such that the anchoring structure is pivoted less than 90° relative to the longitudinal axis;
    tensioning the loop of suture material by pulling on one or both of the two free ends of the length of suture, to approximate the soft tissue with respect to the body cavity as desired
    and wherein said step of fixing is carried out independent from tensioning, pulling or otherwise manipulating the sutures; and
    compressively locking a portion of the length of suture within the lumen of the anchor body.

2. The method as recited in claim 1, and further comprising a step of fastening the two free ends of the length of suture with respect to the anchor body without knots.

3. The method as recited in claim 1, wherein the soft tissue is a tendon, and the body cavity is formed in a bone.

4. The method as recited in claim 1, wherein the step of fixing the anchor body with respect to the body cavity further comprises forming the body cavity, passing the anchor body into the body cavity, and radially expanding the anchoring structure on the anchor body.

5. The method as recited in claim 4, wherein the body cavity is formed in bone and the anchoring structure is provided on a proximal end of the anchor body so as to engage the cortical layer of the bone and to prevent proximal removal of the anchor body from the body cavity.

6. The method as recited in claim 5, wherein the anchoring structure comprises a deployable toggle member.

7. The method of claim 1 wherein compressively locking the portion of the length of suture further comprises displacing a locking plug proximally into the lumen of the anchor body to anchor the portion of the length of suture within the anchor body.

8. A method of securing soft tissue with respect to a bone socket comprising a side wall and an end wall, comprising:
    passing a length of suture material through soft tissue so that a loop of suture material is disposed in the soft tissue, resulting in two free ends;
    threading a tubular shaped anchor with both said free ends, the anchor having a longitudinal axis defining a lumen, wherein the step of threading further comprises distally passing both said free ends through an aperture in an actuatable component and a proximal open end of the lumen, the actuatable component positioned proximally of the lumen;
    inserting the anchor into the bone socket;
    actuating the component of the anchor to affix the anchor in the bone socket, wherein the step of actuating comprises deforming a connecting portion between the anchor and the component in order to pivot the component less than 90° relative to the longitudinal axis;
    tensioning the loop of suture material by pulling on one or both of the two free ends of the length of suture, to approximate the soft tissue with respect to the bone socket as desired wherein said actuating is carried out independent from tensioning, pulling or otherwise manipulating the sutures; and
    compressively locking a portion of the length of suture within the anchor.

9. The method of claim 8 wherein said anchor is positioned on the distal end of an insertion shaft.

10. The method of claim 9 wherein component to be actuated is a ring-shaped member located at a proximal end of the anchor.

11. The method of claim 8 wherein compressively locking the portion of the length of suture within the anchor further comprises displacing a locking plug proximally into the anchor.

* * * * *